US009327110B2

(12) United States Patent
Kramer et al.

(10) Patent No.: US 9,327,110 B2
(45) Date of Patent: May 3, 2016

(54) DEVICES, SYSTEMS AND METHODS FOR THE TARGETED TREATMENT OF MOVEMENT DISORDERS

(75) Inventors: Jeffery M. Kramer, San Francisco, CA (US); Robert M. Levy, Jacksonville, FL (US)

(73) Assignee: St. Jude Medical Luxembourg Holdings SMI S.A.R.L. ("SJM LUX SMI"), Luxembourg (LU)

( * ) Notice: Subject to any disclaimer, the term of this patent is extended or adjusted under 35 U.S.C. 154(b) by 0 days.

(21) Appl. No.: 13/365,163

(22) Filed: Feb. 2, 2012

(65) Prior Publication Data

US 2012/0158094 A1 Jun. 21, 2012

Related U.S. Application Data

(63) Continuation-in-part of application No. 12/607,009, filed on Oct. 27, 2009, now Pat. No. 9,056,197.

(60) Provisional application No. 61/438,895, filed on Feb. 2, 2011.

(51) Int. Cl.
*A61N 1/36* (2006.01)
*A61N 1/05* (2006.01)
(Continued)

(52) U.S. Cl.
CPC ............ *A61N 1/0551* (2013.01); *A61B 5/1118* (2013.01); *A61B 5/4082* (2013.01); *A61N 1/36067* (2013.01); *A61N 1/36071* (2013.01);
(Continued)

(58) Field of Classification Search
CPC .......................... A61N 1/0551; A61N 1/36067

USPC ................................ 607/48–49, 117–118, 46
See application file for complete search history.

(56) References Cited

U.S. PATENT DOCUMENTS

| 525,891 A | 9/1894 | Fricke |
| 3,724,467 A | 4/1973 | Avery et al. |

(Continued)

FOREIGN PATENT DOCUMENTS

| CN | 2401143 Y | 10/2000 |
| CN | 101594907 A | 12/2009 |

(Continued)

OTHER PUBLICATIONS

Kramer et al.; U.S. Appl. No. 13/458,697 entitled "Selective stimulation to modulate the sympathetic nervous system," filed Apr. 27, 2012.

(Continued)

*Primary Examiner* — Alyssa M Alter

(57) ABSTRACT

Devices, systems and methods are provided for the targeted treatment of movement disorders. Typically, the systems and devices are used to stimulate one or more dorsal root ganglia while minimizing or excluding undesired stimulation of other tissues, such as surrounding or nearby tissues, ventral root and portions of the anatomy associated with body regions which are not targeted for treatment. The dorsal root ganglia are utilized in particular due to their specialized role in movement. It is in these areas that sensory fibers are isolated from motor fibers. Sensory fibers are involved in a variety of reflexes that are involved in movement control, and these reflexes can be utilized in the treatment of various movement disorders. Thus, by stimulating sensory fibers in these areas, fundamental reflexes can be affected to lessen the symptoms of movement disorders.

22 Claims, 5 Drawing Sheets

(51) Int. Cl.
  *A61B 5/00*    (2006.01)
  *A61B 5/0488*  (2006.01)
  *A61B 5/11*    (2006.01)

(52) U.S. Cl.
  CPC ............ *A61B 5/0488* (2013.01); *A61B 5/1116* (2013.01); *A61B 5/1123* (2013.01); *A61N 1/36017* (2013.01)

(56) References Cited

U.S. PATENT DOCUMENTS

| | | | |
|---|---|---|---|
| 3,845,770 A | 11/1974 | Theeuwes et al. | |
| 3,916,899 A | 11/1975 | Theeuwes et al. | |
| 4,141,367 A | 2/1979 | Ferreira | |
| 4,232,679 A | 11/1980 | Schulman | |
| 4,298,003 A | 11/1981 | Theeuwes et al. | |
| 4,313,448 A | 2/1982 | Stokes | |
| 4,374,527 A | 2/1983 | Iversen | |
| 4,479,491 A | 10/1984 | Martin | |
| 4,549,556 A | 10/1985 | Tarjan et al. | |
| 4,573,481 A | 3/1986 | Bullara | |
| 4,577,642 A | 3/1986 | Stokes | |
| 4,590,946 A | 5/1986 | Loeb | |
| 4,607,639 A | 8/1986 | Tanagho et al. | |
| 4,739,764 A | 4/1988 | Lue et al. | |
| 4,786,155 A | 11/1988 | Fantone et al. | |
| 4,803,988 A | 2/1989 | Thomson | |
| 4,920,979 A | 5/1990 | Bullara | |
| 4,940,065 A | 7/1990 | Tanagho et al. | |
| 4,950,270 A | 8/1990 | Bowman et al. | |
| 4,976,711 A | 12/1990 | Parins et al. | |
| 5,135,525 A | 8/1992 | Biscoping et al. | |
| 5,270,099 A | 12/1993 | Kamiyama et al. | |
| 5,299,569 A | 4/1994 | Wernicke et al. | |
| 5,344,438 A | 9/1994 | Testerman et al. | |
| 5,358,514 A | 10/1994 | Schulman et al. | |
| 5,370,644 A | 12/1994 | Langberg | |
| 5,411,537 A | 5/1995 | Munshi et al. | |
| 5,411,540 A | 5/1995 | Edell et al. | |
| 5,417,719 A | 5/1995 | Hull et al. | |
| 5,419,763 A | 5/1995 | Hildebrand | |
| 5,458,626 A | 10/1995 | Krause | |
| 5,489,294 A | 2/1996 | McVenes et al. | |
| 5,505,201 A | 4/1996 | Grill et al. | |
| 5,514,175 A | 5/1996 | Kim et al. | |
| 5,584,835 A | 12/1996 | Greenfield | |
| 5,634,462 A | 6/1997 | Tyler et al. | |
| 5,643,330 A | 7/1997 | Holsheimer et al. | |
| 5,702,429 A | 12/1997 | King | |
| 5,711,316 A | 1/1998 | Elsberry et al. | |
| 5,713,922 A | 2/1998 | King | |
| 5,733,322 A | 3/1998 | Starkebaum | |
| 5,741,319 A | 4/1998 | Woloszko et al. | |
| 5,755,750 A | 5/1998 | Petruska et al. | |
| 5,776,170 A | 7/1998 | MacDonald et al. | |
| 5,807,339 A | 9/1998 | Bostrom et al. | |
| 5,824,021 A | 10/1998 | Rise | |
| 5,865,843 A | 2/1999 | Baudino | |
| 5,871,531 A | 2/1999 | Struble | |
| 5,885,290 A | 3/1999 | Guerrero et al. | |
| 5,938,690 A | 8/1999 | Law et al. | |
| 5,948,007 A | 9/1999 | Starkebaum et al. | |
| 5,957,965 A | 9/1999 | Moumane et al. | |
| 5,983,141 A | 11/1999 | Sluijter et al. | |
| 5,984,896 A | 11/1999 | Boyd | |
| 6,002,964 A | 12/1999 | Feler et al. | |
| 6,044,297 A | 3/2000 | Sheldon et al. | |
| 6,045,532 A | 4/2000 | Eggers et al. | |
| 6,051,017 A | 4/2000 | Loeb et al. | |
| 6,104,957 A * | 8/2000 | Alo et al. ........................ 607/46 | |
| 6,120,467 A | 9/2000 | Schallhorn | |
| 6,161,048 A | 12/2000 | Sluijter et al. | |
| 6,175,764 B1 | 1/2001 | Loeb et al. | |
| 6,181,965 B1 | 1/2001 | Loeb et al. | |
| 6,185,455 B1 | 2/2001 | Loeb et al. | |
| 6,205,359 B1 | 3/2001 | Boveja | |
| 6,208,902 B1 | 3/2001 | Boveja | |
| 6,214,016 B1 | 4/2001 | Williams et al. | |
| 6,259,952 B1 | 7/2001 | Sluijter et al. | |
| 6,298,256 B1 | 10/2001 | Meyer | |
| 6,314,325 B1 | 11/2001 | Fitz | |
| 6,319,241 B1 | 11/2001 | King et al. | |
| 6,349,233 B1 | 2/2002 | Adams | |
| 6,353,762 B1 | 3/2002 | Baudino et al. | |
| 6,356,786 B1 | 3/2002 | Rezai et al. | |
| 6,360,750 B1 | 3/2002 | Gerber et al. | |
| 6,366,814 B1 | 4/2002 | Boveja et al. | |
| 6,393,325 B1 | 5/2002 | Mann et al. | |
| 6,413,255 B1 | 7/2002 | Stern | |
| 6,425,887 B1 | 7/2002 | McGuckin et al. | |
| 6,438,423 B1 | 8/2002 | Rezai et al. | |
| 6,440,090 B1 | 8/2002 | Schallhorn | |
| 6,466,821 B1 | 10/2002 | Pianca et al. | |
| 6,493,588 B1 | 12/2002 | Malaney et al. | |
| 6,510,347 B2 | 1/2003 | Borkan | |
| 6,512,958 B1 | 1/2003 | Swoyer et al. | |
| 6,516,227 B1 | 2/2003 | Meadows et al. | |
| 6,517,542 B1 | 2/2003 | Papay et al. | |
| 6,522,926 B1 | 2/2003 | Kieval et al. | |
| 6,535,767 B1 | 3/2003 | Kronberg | |
| 6,582,441 B1 | 6/2003 | He et al. | |
| 6,587,725 B1 | 7/2003 | Durand et al. | |
| 6,605,094 B1 | 8/2003 | Mann et al. | |
| 6,606,521 B2 | 8/2003 | Paspa et al. | |
| 6,611,715 B1 | 8/2003 | Boveja | |
| 6,625,496 B1 | 9/2003 | Ollivier | |
| 6,638,276 B2 | 10/2003 | Sharkey et al. | |
| 6,658,302 B1 | 12/2003 | Kuzma et al. | |
| 6,714,822 B2 | 3/2004 | King et al. | |
| 6,748,276 B1 | 6/2004 | Daignault, Jr. et al. | |
| 6,754,539 B1 | 6/2004 | Erickson et al. | |
| 6,788,975 B1 | 9/2004 | Whitehurst et al. | |
| 6,792,318 B2 | 9/2004 | Chitre et al. | |
| 6,832,115 B2 | 12/2004 | Borkan | |
| 6,835,194 B2 | 12/2004 | Johnson et al. | |
| 6,839,588 B1 | 1/2005 | Rudy | |
| 6,849,075 B2 | 2/2005 | Bertolero et al. | |
| 6,862,479 B1 | 3/2005 | Whitehurst et al. | |
| 6,871,099 B1 | 3/2005 | Whitehurst et al. | |
| 6,873,342 B2 | 3/2005 | Perry et al. | |
| 6,889,094 B1 | 5/2005 | Kuzma et al. | |
| 6,901,287 B2 | 5/2005 | Davis et al. | |
| 6,902,547 B2 | 6/2005 | Aves et al. | |
| 6,909,917 B2 | 6/2005 | Woods et al. | |
| 6,928,320 B2 * | 8/2005 | King ................................ 607/5 | |
| 6,971,391 B1 | 12/2005 | Wang et al. | |
| 6,978,180 B2 | 12/2005 | Tadlock | |
| 7,047,082 B1 | 5/2006 | Schrom et al. | |
| 7,096,070 B1 | 8/2006 | Jenkins et al. | |
| 7,127,287 B2 | 10/2006 | Duncan et al. | |
| 7,181,289 B2 | 2/2007 | Pflueger et al. | |
| 7,333,857 B2 | 2/2008 | Campbell | |
| 7,337,005 B2 | 2/2008 | Kim et al. | |
| 7,337,006 B2 | 2/2008 | Kim et al. | |
| 7,447,546 B2 | 11/2008 | Kim et al. | |
| 7,450,993 B2 | 11/2008 | Kim et al. | |
| 7,502,651 B2 | 3/2009 | Kim et al. | |
| 7,580,753 B2 | 8/2009 | Kim et al. | |
| 8,082,039 B2 | 12/2011 | Kim et al. | |
| 2001/0003799 A1 | 6/2001 | Boveja | |
| 2001/0006967 A1 | 7/2001 | Crain et al. | |
| 2002/0064841 A1 | 5/2002 | Klemic et al. | |
| 2002/0077684 A1 | 6/2002 | Clemens et al. | |
| 2002/0087113 A1 | 7/2002 | Hartlaub | |
| 2002/0099430 A1 | 7/2002 | Verness | |
| 2002/0116030 A1 | 8/2002 | Rezai | |
| 2002/0128694 A1 | 9/2002 | Holsheimer | |
| 2002/0147486 A1 | 10/2002 | Soukup et al. | |
| 2002/0198527 A1 | 12/2002 | Muckter | |
| 2003/0018367 A1 | 1/2003 | Dilorenzo | |
| 2003/0023241 A1 | 1/2003 | Drewry et al. | |
| 2003/0045919 A1 | 3/2003 | Swoyer et al. | |
| 2003/0069569 A1 | 4/2003 | Burdette et al. | |
| 2003/0078633 A1 | 4/2003 | Firlik et al. | |

(56) References Cited

U.S. PATENT DOCUMENTS

| | | |
|---|---|---|
| 2003/0088301 A1 | 5/2003 | King |
| 2003/0100933 A1 | 5/2003 | Ayal et al. |
| 2003/0114905 A1 | 6/2003 | Kuzma |
| 2003/0130577 A1 | 7/2003 | Purdy et al. |
| 2003/0144657 A1 | 7/2003 | Bowe et al. |
| 2003/0144709 A1 | 7/2003 | Zabara et al. |
| 2003/0181958 A1 | 9/2003 | Dobak, III |
| 2003/0187490 A1 | 10/2003 | Gliner |
| 2003/0195602 A1 | 10/2003 | Boling |
| 2003/0220677 A1 | 11/2003 | Doan et al. |
| 2004/0015202 A1 | 1/2004 | Chandler et al. |
| 2004/0019359 A1 | 1/2004 | Worley et al. |
| 2004/0019369 A1 | 1/2004 | Duncan et al. |
| 2004/0059404 A1 | 3/2004 | Bjorklund et al. |
| 2004/0116977 A1 | 6/2004 | Finch et al. |
| 2004/0122360 A1 | 6/2004 | Waldhauser et al. |
| 2004/0122477 A1 | 6/2004 | Whitehurst et al. |
| 2004/0122497 A1 | 6/2004 | Zhang et al. |
| 2004/0122498 A1 | 6/2004 | Zhang et al. |
| 2004/0147992 A1 | 7/2004 | Bluger et al. |
| 2004/0210290 A1 | 10/2004 | Omar-Pasha |
| 2004/0215286 A1 | 10/2004 | Stypulkowski |
| 2004/0230273 A1 | 11/2004 | Cates et al. |
| 2004/0230280 A1 | 11/2004 | Cates et al. |
| 2004/0243210 A1 | 12/2004 | Morgan et al. |
| 2005/0027338 A1 | 2/2005 | Hill |
| 2005/0033295 A1 | 2/2005 | Wisnewski |
| 2005/0033393 A1 | 2/2005 | Daglow |
| 2005/0038489 A1 | 2/2005 | Grill |
| 2005/0070982 A1 | 3/2005 | Heruth et al. |
| 2005/0080325 A1 | 4/2005 | Erickson |
| 2005/0090885 A1 | 4/2005 | Harris et al. |
| 2005/0096718 A1 | 5/2005 | Gerber et al. |
| 2005/0149154 A1 | 7/2005 | Cohen et al. |
| 2005/0154437 A1 | 7/2005 | Williams |
| 2005/0159799 A1 | 7/2005 | Daglow et al. |
| 2005/0203599 A1 | 9/2005 | Garabedian et al. |
| 2005/0222647 A1 | 10/2005 | Wahlstrand et al. |
| 2005/0251237 A1 | 11/2005 | Kuzma et al. |
| 2006/0004364 A1 | 1/2006 | Green et al. |
| 2006/0009820 A1 | 1/2006 | Royle |
| 2006/0041295 A1 | 2/2006 | Osypka |
| 2006/0052828 A1* | 3/2006 | Kim et al. ............ 607/3 |
| 2006/0052836 A1 | 3/2006 | Kim et al. |
| 2006/0052856 A1 | 3/2006 | Kim et al. |
| 2006/0064150 A1 | 3/2006 | Heist et al. |
| 2006/0089609 A1 | 4/2006 | Bleich et al. |
| 2006/0089696 A1 | 4/2006 | Olsen et al. |
| 2006/0094976 A1* | 5/2006 | Bleich ................. 600/547 |
| 2006/0095088 A1 | 5/2006 | DeRidder |
| 2006/0155344 A1 | 7/2006 | Rezai et al. |
| 2006/0161235 A1 | 7/2006 | King |
| 2006/0167525 A1 | 7/2006 | King |
| 2006/0195169 A1 | 8/2006 | Gross et al. |
| 2006/0200121 A1 | 9/2006 | Mowery |
| 2006/0206118 A1 | 9/2006 | Kim et al. |
| 2006/0241716 A1 | 10/2006 | Finch et al. |
| 2006/0247750 A1 | 11/2006 | Seifert et al. |
| 2007/0043400 A1 | 2/2007 | Donders et al. |
| 2007/0060954 A1 | 3/2007 | Cameron et al. |
| 2007/0123954 A1 | 5/2007 | Gielen et al. |
| 2007/0179579 A1 | 8/2007 | Feler et al. |
| 2007/0213671 A1 | 9/2007 | Hiatt |
| 2007/0255366 A1 | 11/2007 | Gerber et al. |
| 2007/0270928 A1 | 11/2007 | Erlebacher |
| 2007/0276319 A1 | 11/2007 | Betts |
| 2008/0009927 A1 | 1/2008 | Vilims |
| 2008/0033431 A1 | 2/2008 | Jung et al. |
| 2008/0039916 A1 | 2/2008 | Colliou et al. |
| 2008/0103572 A1 | 5/2008 | Gerber |
| 2008/0103579 A1 | 5/2008 | Gerber |
| 2008/0103580 A1 | 5/2008 | Gerber |
| 2008/0119711 A1 | 5/2008 | Nikumb et al. |
| 2008/0140152 A1 | 6/2008 | Imran et al. |
| 2008/0140153 A1 | 6/2008 | Burdulis |
| 2008/0140169 A1 | 6/2008 | Imran |
| 2008/0147156 A1 | 6/2008 | Imran |
| 2008/0154349 A1 | 6/2008 | Rossing et al. |
| 2008/0167698 A1 | 7/2008 | Kim et al. |
| 2008/0183221 A1 | 7/2008 | Burdulis |
| 2008/0183257 A1 | 7/2008 | Imran et al. |
| 2008/0188916 A1 | 8/2008 | Jones et al. |
| 2009/0204173 A1 | 8/2009 | Fang et al. |
| 2009/0210041 A1 | 8/2009 | Kim et al. |
| 2009/0248095 A1 | 10/2009 | Schleicher et al. |
| 2009/0270960 A1 | 10/2009 | Zhao et al. |
| 2009/0299444 A1 | 12/2009 | Boling |
| 2010/0121408 A1 | 5/2010 | Imran et al. |
| 2010/0137938 A1 | 6/2010 | Kishawi et al. |
| 2010/0179562 A1* | 7/2010 | Linker et al. ............ 606/129 |
| 2010/0191307 A1 | 7/2010 | Fang et al. |
| 2010/0249875 A1 | 9/2010 | Kishawi et al. |
| 2010/0292769 A1 | 11/2010 | Brounstein et al. |
| 2011/0184486 A1 | 7/2011 | De Ridder |
| 2011/0257693 A1 | 10/2011 | Burdulis |
| 2011/0276056 A1 | 11/2011 | Grigsby et al. |
| 2012/0197370 A1 | 8/2012 | Kim et al. |
| 2012/0310140 A1 | 12/2012 | Kramer et al. |
| 2013/0345783 A1 | 12/2013 | Burdulis |
| 2014/0200625 A1 | 7/2014 | Kim et al. |
| 2015/0165193 A1 | 6/2015 | Imran |

FOREIGN PATENT DOCUMENTS

| | | |
|---|---|---|
| CN | 101678204 A | 3/2010 |
| EP | 0779080 A | 6/1997 |
| EP | 1304135 A2 | 4/2003 |
| EP | 2756864 A1 | 7/2014 |
| JP | 03041191 B2 | 6/1991 |
| JP | H06-218064 A | 8/1994 |
| JP | 8500996 A | 2/1996 |
| JP | 8080353 A | 3/1996 |
| JP | 10243954 A | 9/1998 |
| JP | 2004512105 | 4/2004 |
| JP | 2006523215 | 10/2004 |
| JP | 2005516697 | 6/2005 |
| JP | 2006508768 | 3/2006 |
| JP | 2008526299 | 7/2008 |
| JP | 2009539425 A | 11/2009 |
| JP | 2009539426 A | 11/2009 |
| WO | WO 02/096512 A1 | 12/2002 |
| WO | WO 03/018113 A1 | 3/2003 |
| WO | WO 03/043690 A1 | 5/2003 |
| WO | WO 03/063692 | 8/2003 |
| WO | WO 03/066154 A2 | 8/2003 |
| WO | WO 03/084433 A2 | 10/2003 |
| WO | WO 03/090599 A2 | 11/2003 |
| WO | WO 2005/092432 A1 | 10/2005 |
| WO | WO 2006/033039 A1 | 3/2006 |
| WO | WO 2006/084635 A2 | 8/2006 |
| WO | WO 2008/070809 A2 | 6/2008 |
| WO | WO 2009/134350 A2 | 11/2009 |
| WO | WO 2010/062622 A2 | 6/2010 |
| WO | WO 2010/132816 A2 | 11/2010 |

OTHER PUBLICATIONS

Kim et al.; U.S. Appl. No. 13/550,439 entitled "Methods for Stimulating a Dorsal Root Ganglion," filed Jul. 16, 2012.
Wedley et al. Handbook of Clinical Techniques in the Management of Chronic Pain. Taylor & Francis; pp. 17-19. Nov. 27, 1996.
Kim et al.; U.S. Appl. No. 13/706,100 entitled "Neurostimulation Methods and Systems," filed Dec. 5, 2012.
Kishawi et al.; U.S. Appl. No. 13/753,326 entitled "Pain management with stimulation subthreshold to parasthesia," filed Jan. 29, 2013.
Abdulla et al.; Axotomy- and autotomy-induced changes in the excitability of rat dorsal root ganglion neurons; J Neurophysiol; 85(2); pp. 630-643; Feb. 2001.
Advanced Neuromodulation Systems, Inc. (ANSI) Research Briefing dated Aug. 20, 2004 by Stephens Inc. Investment Bankers pp. 1-4.
Advanced Neuromodulation Systems, Inc. (ANSI) Research Bulletin dated Jul. 2, 2004 by Stephens Inc. Investment Bankers pp. 1-7.

(56) References Cited

OTHER PUBLICATIONS

Advanced Neuromodulation Systems, Inc. (ANSI) Research Bulletin dated Jul. 27, 2004 by Stephens Inc. Investment Bankers pp. 1-9.
Advanced Neuromodulation Systems, Inc. Equity Research dated Jan. 16, 2003 by Pacific Growth Equities pp. 1-8.
Alo, Kenneth M. New Trends in Neuromodulation for the Management of Neuropathic Pain. Neurosurgery. Apr. 2002. 50 (4): 690-703.
Aoki, Yasuchika et al. Distribution and Immunocytochemical Characterization of Dorsal Root Ganglion Neurons Innervating the Lumbar Intervertebral Disc in Rats: A Review. Life Sciences. Apr. 2004. 74 (21): 2627-2642.
Askar, Zahid, et al. Scott Wiring for Direct Repair of Lumbar Spondylolysis. Spine. Feb. 2003. 28 (4): 354-357.
Baba, Hiroshi et al. Peripheral Inflammation Facilitates A? Fiber-Mediated Synaptic Input to the Substantia Gelatinosa of the Adult Rat Spinal Cord. The Journal of Neuroscience. Jan. 1999. 19 (2): 859-867.
Bajwa, Zahid H. et al. Herpetic Neuralgia: Use of Combination Therapy for Pain Relief in Acute and Chronic Herpes Zoster. Geriatrics. Dec. 2001; 56 (12): 18-24.
Barendse, G.A. et al. Randomized Controlled Trial of Percutaneous Intradiscal Radiofrequency Thermocoagulation for Chronic Discogenic Back Pain: Lack of Effect From a 90-Second 70 C Lesion. Spine. 26 (3): 287-92. (Abstract Only). Feb. 1, 2001.
Barlocher, C.B. et al. Kryorhizotomy: An Alternative Technique for Lumbar Medial Branch Rhizotomy in Lumber Facet Syndrome. J. Neurosurg. 98 (1): 14-20. (Abstract Only). Jan. 2003.
Blau, A. et al. Characterization and Optimization of Microelectrode Arrays for In Vivo Nerve Signal Recording and Stimulation. Biosens Bioelectron. 12 (9-10): 883-92. (Abstract Only). Nov. 1997.
Boston Scientific A Neuromodulation Primer dated Jun. 9, 2004 in Medical Supplies and Devices, published by Susquehanna Financial Group, LLLP pp. 1-17.
Brammah, T.B. et al. . Syringomyelia as a Complication of Spinal Arachnoiditis. Spine. 19 (22): 2603-5. (Abstract Only). Nov. 15, 1994.
Braverman D.L. et al. Using Gabapentin to Treat Failed Back Surgery Syndrome Caused by Epidural Fibrosis: A Report of 2 Cases. Arch Phys Med Rehabil. 82 (5): 691-3. (Abstract Only). May 2001.
Burton et al.; The organization of the seventh lumbar spinal ganglion of the cat; J Comp Neurol.; 149(2); pp. 215-232; May 15, 1973.
Carlton, Susan M. et al. Tonic Control of Peripheral Cutaneous Nociceptors by Somatostatin Receptors. Journal of Neuroscience. 21 (11): 4042-4049. Jun. 1, 2001.
Chaplan, S.R. et al. Quantitative Assessment of Tactile Allodynia in the Rat Paw. Journal of Neuroscience Methods. 53 (1): 55-63. Jul. 1994.
Cho, J. Percutaneo Radiofrequency Lumbar Facet Rhizotomy in Mechanical Low Back Pain Syndrome. Stereotact Funct Neurosurg. 68 (1-4): 212-7. (Abstract Only). (month unavailable) 1997.
Clark, Robert K. "Anatomy and physiology: understanding the human body"; Jones & Bartlett Publishers; Sudbury, MA; ISBN 0-7637-4816-6; Chapter 12; pp. 213-215; Feb. 28, 2005.
Crampon, M.-A. et al. Nerve Cuff Electrode With Shape Memory Alloy Armature: Design and Fabrication. Bio-Medical Materials and Engineering. 12 (4): 397-410. (month unavailable) 2002.
Cuoco, Jr., Frank A. et al. Measurement of External Pressures Generated by Nerve Cuff Electrodes. IEEE Transactions on Rehabilitation Engineering. 8 (1): 35-41. Mar. 2000.
Cyberonics, Inc. Equity Research dated Jan. 16, 2003 by Pacific Growth Equities pp. 1-14.
Denny, N.M. et al. Evaluation of an Insulated Tuohy Needle System for the Placement of Interscalene Brachial Plex Catheters. Anaesthesia. 58 (6): 554-7. (Abstract Only). Jun. 2003.
Dreyfuss, Paul et al. Efficacy and Validity of Radiofrequency Neurotomy for Chronic Lumbar Zygapophysial Joint Pain. Spine. 25 (10): 1270-1277. May 15, 2000.
Dubuisson, D. Treatment of Occipital Neuralgia by Partial Posterior Rhizotomy at C1-3. J Neurosurg. 82 (4): 581-6. (Abstract Only). Apr. 1995.
Eschenfelder, Sebastian et al. Dorsal Root Section Elicits Signs of Neuropathic Pain Rather than Reversing Them in Rats With L5 Spinal Nerve Injury. Pain. 87 (2): 213-219. Aug. 2000.
Firth, Ava et al. Development of a Scale to Evaluate Postoperative Pain in Dogs. J Am Vet Med Assoc. 214 (5): 651-659. Mar. 1, 1999.
Garcia Cosamalon, P. J. et al. Dorsal Percutaneo Radiofrequency Rhizotomy Guided With CT Scan in Intercostal Neuralgias. Technical note. Acta Neurochir (Wien). 109 (3-4): 140-1. (month unavailable) 1991.
Giorgi, C. et al. Surgical Treatment of Glossopharyngeal Neuralgia and Pain From Cancer of the Nasopharynx. A 20-Year Experience. J Neurosurg. 61 (5): 952-5. (Abs. Only). Nov. 1984.
Gocer, A.I. et al. Percutaneous Radiofrequency Rhizotomy of Lumbar Spinal Facets the Results of 46 cases. Neurosurg Rev. 20 (2): 114-6. (Abstract Only). (month unavailable) 1997.
Haller, H. et al. Treatment of Chronic Neuropathic Pain After Traumatic Central Cervical Cord Lesion with Gabapentin. Journal of Neural Transmission. 110 (9): 977-981. Sep. 2003.
Herron, L.D. Selective Nerve Root Block in Patient Selection for Lumbar Surgery: Surgical Results. J Spinal Disord. 2 (2): 75-9. (Abstract Only). Jun. 1989.
Higuchi, Yoshinori, et al. Exposure of the Dorsal Root Ganglion in Rats to Pulsed Radiofrequency Currents Activates Dorsal Horn Lamina I and II Neurons. Neurosurgery. 50 (4): 850-856. Apr. 2002.
Holsheimer, J. et al. Effects of Electrode Geometry and Combination on Nerve Fibre Selectivity in Spinal Cord Stimulation. Medical & Biological Engineering & Computing. 33 (5): 676-682. Sep. 1995.
Igarashi, T. et al. Lysis of Adhesions and Epidural Injection of Steroid/Local Anaesthetic During Epiduroscopy Potentially Alleviate Low Back and Leg Pain in Elderly Patients With Lumbar Spinal Stenosis. British Journal of Anaesthesia. 93 (2): 181-7.Aug. 2004.
Julius, David et al. Molecular Mechanisms of Nociception. Nature. 413 (6852): 203-210. Sep. 13, 2001.
Kanpolat, Yucel et al. Percutaneo Controlled Radiofrequency Trigeminal Rhizotomy for the Treatment of Idiopathic Trigeminal Neuralgia: 25-Year Experience with 1600 Patients. Neurosurgery. 48 (3): 524-534. Mar 2001.
Kapadia, N.P. et al. Gabapentin for Chronic Pain in Spinal Cord Injury: A Case Report. Arch Phys Med Rehabil. 81 (10): 1439-41. (Abstract Only). Oct. 2000.
Kapoor, Vibhu et al. Refractory Occipital Neuralgia: Preoperative Assessment With CT-Guided Nerve Block Prior to Dorsal Cervical Rhizotomy. American Journal of Neuroradiology. 24 (10): 2105-10. Nov.-Dec. 2003.
Karai, Laszlo et al. Deletion of Vanilloid Receptor 1-Expressing Primary Afferent Neurons for Pain Control. Journal of Clinical Investigation. 113 (9): 1344-1352. May 2004.
Kline, David G. et al. Management and Results of Sciatic Nerve Injuries: a 24-Year Experience. Journal of Neurosurgery. 89 (1): 13-23. Jul. 1998.
Kobayashi, Shigeru et al. Pathology of Lumbar Nerve Root Compression Part 1: Intraradicular Inflammatory Changes Induced by Mechanical Compression. Journal of Orthopaedic Research. 22 (1): 170-179. Jan 2004.
Kobayashi, Shigeru et al. Pathology of Lumbar Nerve Root Compression Part 2: Morphological and Immunohistochemical Changes of Dorsal Root Ganglion. Journal of Orthopaedic Research. 22 (1): 180-188. Jan. 2004.
Kocsis et al.; NR2B receptors are involved in the mediation of spinal segmental reflex potentials but not in the cumulative motoneuronal depolarization in vitro; Brain Research Bulletin, Elsevier Science Ltd.; vol. 64; No. 2; pp. 133-138; Aug. 30, 2004.
Koszewski, W. et al. [The Drez Lesion as an Effective Treatment for Chronic Hypothetically Post-Herpetic Neuropathic Pain. Case Report and Review of Literature]. Neurol Neurochir Pol. 37 (4): 943-53. (Abstract Only). (month unavailable) 2003.
Lawrence, Stephen M. et al. Long-Term Biocompatibility of Implanted Polymer-Based Intrafascicular Electrodes. Journal of Biomedical Materials Research. Article first publ. online: 63 (5): 501-506. Jul. 31, 2002.
Lee, In-Seop et al. Characterization of Iridium Film as a Stimulating Neural Electrode. Biomaterials. 23 (11): 2375-2380. Jun. 2002.

(56) References Cited

OTHER PUBLICATIONS

Lew, Henry L. et al. Preganglionic Approach to Transforaminal Epidural Steroid Injections. Am. J. Phys. Med. Rehabil. 83 (5): 378. May 2004.
Lopez et al.; Excitatory and inhibitory effects of serotonin on spinal nociceptive reflexes are mediated by 5-HT2 and 5-HT1B receptors; (Database Biosis Biosciences information service, Philadelphia, PA, US, XP002567533, accession No. PREV200100573757); Abstract; (month unavailable) 2001.
Ma et al.; Enhanced excitability of dissociated primary sensory neurons after chronic compression of the dorsal root ganglion in the rat; Pain; 113(1-2); pp. 106-112; Jan. 2005.
Maher, C.O. et al. Lateral Exit-Zone Stenosis and Lumbar Radiculopathy. J Neurosurg. 90 (1 Suppl): 52-8. Jan. 1999. (Abstract Only).
Mailley, Sophie et al. Thin Film Platinum Cuff Electrodes for Neurostimulation: In Vitro Approach of Safe Neurostimulation Parameters. Bioelectrochemistry. 63(1-20: 359-364. Jun. 2004.
Masini, Michelle et al. Activated Pyrolytic Carbon Tip Pacing Leads: An Alternative to Steroid-Eluting Pacing Leads? PACE. 19(11 Pt 2): 1832-1835. Nov. 1996.
Medtronic, Inc. Equity Research dated Dec. 18, 2002 by Pacific Growth Equities pp. 1-20.
Medtronic. Analysis of Sales/Earnings-F1Q05: Many Gives and Takes in the Quarter dated Aug. 20, 2004 by Morgan Stanley pp. 1-25.
Methods of Placement of Neurostimulation Lead, Infusion, Catheter, and/or Sensor Via Peripheral Vasculature. From IP.com PriorArtDatabase—Apr. 10, 2003—#000012136 http://www.priorartdatabase.com/IPCOM/000012136.
Modern Ideas: The Gate Control Theory of Chronic Pain. Spine-Health.com: Your Comprehensive Resource for Back Pain. http://www.spine-health.com/topics/cd/pain/chronic_pain_theories/chronic_pain_theory02.html (accessed Feb. 24, 2006); 2 pages.
Mond, Harry G. et al. Implantable Transveno Pacing Leads: The Shape of Things to Come. PACE. 27: 887-893. Jun. 2004.
Monti, Enrico. Peripheral Nerve Stimulation: A Percutaneous Minimally Invasive Approach. Neuromodulation. 7 (3): 193. Jul. 2004. (Abstract Only).
Myles et al.; Effects of different methods of peripheral nerve repair on the number and distribution of muscle afferent neurons in rat dorsal root ganglion; J Neurosurg; 77(3); pp. 457-462; Sep. 1992.
Nannini et al.; Muscle recruitment with intrafascicular electrodes; IEEE Trans on Biomedical Engineering; vol. 38; No. 8; pp. 769-776; Aug. 1991.
Naples, Gregory G. A Spiral Nerve Cuff Electrode for Peripheral Nerve Stimulation. IEEE Transactions on Biomedical Engineering. 35 (11): 905-916. Nov. 1988.
Narozny, Martin et al. Therapeutic Efficacy of Selective Nerve Root Blocks in the Treatment of Lumbar Radicular Leg Pain. Swiss Med Wkly. 131(5-6): 75-80. Feb. 2001.
Nashold, Blaine S. et al. Peripheral Nerve Stimulation for Pain Relief Using a Multicontact Electrode System. Technical note. Journal of Neurosurgery. 51 (6): 872-873. Dec. 1979.
Nashold, Blaine S. et al. Long-Term Pain Control by Direct Peripheral-Nerve Stimulation. The Journal of Bone and Joint Surgery. 64 (1): 1-10. Jan. 1982.
Neumann, Simona et al. Regeneration of Sensory Axons Within the Injured Spinal Cord Induced by Intraganglionic cAMP Elevation. Neuron. 34 (6): 885-93. Jun. 13, 2002.
Nielson, K.D. et al. Peripheral Nerve Injury From Implantation of Chronic Stimulating Electrodes for Pain Control. Surg Neurol. 5 (1): 51-3. (Abstract Only).Jan. 1976.
North, Richard B. et al. Dorsal Root Ganglionectomy for Failed Back Surgery Syndrome: A 5-Year Follow-Up Study. J Neurosurg. 74(2): 236-242. Feb. 1991.
North, Richard B. et al. Chapter 123: Current Concepts in the Neurosurgical Management of Persistent Pain (pp. 1634-1637). Operative Neurosurgical Techniques 4th Edition (Henry H. Schmidek et al. eds.). Philadelphia: W.B. Saunders Company. Publ. date: Aug. 18, 2000.

Nygaard, Oystein P. et al. The Function of Sensory Nerve Fibers in Lumbar Radiculopathy: Use of Quantitative Sensory Testing in the Exploration of Different Populations of Nerve Fibers and Dermatomes. Spine. 23 (3): 348-352. Feb. 1, 1998.
Obata, K. et al. Activation of Extracellular Signal-Regulated Protein Kinase in the Dorsal Root Ganglion Following Inflammation Near the Nerve Cell Body. Neuroscience. 126 (4): 1011-1021. Accepted Apr. 22, 2004.
Obata, Koichi, et al. Expression of Neurotrophic Factors in the Dorsal Root Ganglion in a Rat Model of Lumbar Disc Herniation. Pain. 99 (1-2): 121-132. Sep. 2002.
Olby, Natasha J. et al. Development of a Functional Scoring System in Dogs With Acute Spinal Cord Injuries. Am J Vet Res. 62(10): 1624-1628. Oct. 2001.
Parlier-Cuau, Caroline et al. Symptomatic Lumbar Facet Joint Synovial Cysts: Clinical Assessment of Facet Joint Steroid Injection After 1 and 6 Months and Long-Term Follow-Up in 30 Patients. Radiology. 210 (2): 509-513. Feb. 1999.
Pedrolli, C. et al. [Dorsolumbar Arachnoid Cysts. A Case Report]. Recenti Prog Med. 81 (11): 699-701. Nov. 1990. (Abstract Only).
Prats-Galino et al.; Representations of hindlimb digits in rat dorsal root ganglia; J Comp Neurol; 408(1); pp. 137-145; May 24, 1999.
Rodriguez, Francisco J. et al. Polyimide Cuff Electrodes for Peripheral Nerve Stimulation. Journal of Neuroscience Methods. 98 (2): 105-118. Jun. 1, 2000.
Rokugo, Tomoyuki et al. A Histochemical Study of Substance P in the Rat Spinal Cord: Effect of Transcutaneo Electrical Nerve Stimulation. J Nippon Med Sch. 69 (5): 428-433. Oct. 2002.
Romero, E. et al. Neural Morphological Effects of Long-Term Implantation of the Self-Sizing Spiral Cuff Nerve Electrode. Medical & Biological Engineering & Computing. 39 (1): 90-100. Jan. 2001.
Rongstad, K. et al. Popliteal Sciatic Nerve Block for Postoperative Analgesia. Foot Ankle Int. 17 (7): 378-82. Jul. 1996. (Abstract Only).
Ruetten, S. et al. Endoscopic Surgery of the Lumbar Epidural Space (Epiduroscopy): Results of Therapeutic Intervention in 93 Patients. Minim Invasive Neurosurg. 46 (1): 1-4. Feb. 2003. (Abstract Only).
Sairyo, K. et al. A New Endoscopic Technique to Decompress Lumbar Nerve Roots Affected by Spondylolysis. Technical Note. J Neurosurg. 98(3): 290-3. Apr. 2003. (Abstract Only).
Salame, K. et al. Surgical Treatment of Spasticity by Selective Posterior Rhizotomy 30 Years Experience. Isr Med Assoc J. 5 (8): 543-6. Aug. 2003. (Abstract Only).
Saris, S.C. et al. Sacrococcygeal Rhizotomy for Perineal Pain. Neurosurgery. 19 (5): 789-93. Nov. 1986. (Abstract Only).
Sauvage, P.J. et al. Intraspinal Synovial Cysts of the Lumbar Spine: Imaging Findings and Treatment by Percutaneo Steroid Injection. Review of 13 Cases. [Kystes Synoviaux Intraspinaux Lombaires: Imagerie et Traitement Par Infiltration. A Propos De. (month unavail.) 2000.
Schwartzman, Robert J. et al. Neuropathic Central Pain: Epidemiology, Etiology, and Treatment Options. Arch Neurol. 58 (10): 1547-1550. Oct. 2001.
Sedan, R. et al. Therapeutic Electrical Neurostimulation. French Language Society of Neurosurgery—28th Annual Congress—Athens, May 29-30, 1978. Neurochirurgie. 24: 3-8, Suppl. 1 (in French with English Summary pp. 121-125.).
Sheth, Rishi N. et al. Mechanical Hyperalgesia After an L5 Ventral Rhizotomy or an L5 Ganglionectomy in the Rat. Pain. 96: 63-72. Mar. 2002.
Siddall, Philip J. et al. Persistent Pain as a Disease Entity: Implications for Clinical Management. Anesth Analg. 99: 510-20. Aug. 2004.
Silvers, H.R. Lumbar Percutaneo Facet Rhizotomy. Spine. 15 (1): 36-40. Jan. 1990. (Abstract Only).
Slappendel, R. et al. The efficacy of Radiofrequency Lesioning of the Cervical Spinal Dorsal Root Ganglion in a Double Blinded Randomized Study: No difference Between 40 Degrees C. and 67 Degrees C. Treatments. Pain. 73 (2): 159-63. Nov. 1997. (Abstract Only).
Sluijter, Menno E. et al. The Effects of Pulsed Radiofrequency Fields Applied to the Dorsal Root Ganglion—A Preliminary Report. The Pain Clinic. 11 (2): 109-117. (month unavailable) 1998.

(56) References Cited

OTHER PUBLICATIONS

Smith, H.P. et al. Radiofrequency Neurolysis in a Clinical Model: Neuropathological Correlation. J Neurosurg. 55 (2): 246-53. Aug. 1981. (Abstract Only).
Spaic, M. et al. Drez Surgery on Con Medullaris (After Failed Implantation of Vascular Omental Graft) for Treating Chronic Pain Due to Spine (Gunshot) Injuries. Acta Neurochir(Wein). 141(12): 1309-1312. (month unavailable) 1999.
Spaic, M. et al. Microsurgical DREZotomy for Pain of Spinal Cord and Cauda Equina Injury Origin: Clinical Characteristics of Pain and Implications for Surgery in a Series of 26 Patients. Acta Neurochir (Wien). 144 (5): 453-462. May 2002.
Stanton-Hicks, M. et al. Stimulation of the Central and Peripheral Nervo System for the Control of Pain. Journal of Clinical Neurophysiology. 14 (1): 46-62. Jan. 1997.
Steinbok, P. et al. Complications After Selective Posterior Rhizotomy for Spasticity in Children With Cerebral Palsy. Pediatr Neurosurg. 28 (6): 300-13. Jun. 1998. (Abstract Only).
Stolker, Robert J. et al. The Treatment of Chronic Thoracic Segmental Pain by Radiofrequency Percutaneo Partial Rhizotomy. J Neurosurg. 80(6): 986-992. Jun. 1994.
Strait, T.A. et al. Intraspinal Extradural Sensory Rhizotomy in Patients With Failure of Lumbar Disc Surgery. J Neurosurg. 54(2): 193-6. Feb. 1981. (Abstract Only).
Taha, J.M. et al. Long-Term Results of Radiofrequency Rhizotomy in the Treatment of Cluster Headache. Headache. 35 (4): 193-6. Apr. 1995. (Abstract Only).
Taub, Arthur et al. Dorsal Root Ganglionectomy for Intractable Monoradicular Sciatica: A Series of 61 Patients. Stereotact Funct Neurosurg. 65 (1-4): 106-110. (month unavailable) 1995.
Uematsu, Sumio. Chapter 106: Percutaneo Electrothermocoagulation of Spinal Nerve Trunk, Ganglion, and Rootlets (pp. 1207-1221). Operative Neurosurgical Techniques, Indications, Methods and Results 2nd edition. (Henry H. Schmidek et al. eds.). (month unavail.) 1988.
Van Zundert, Jan et al. Pulsed Radiofrequency in Chronic Pain Management: Looking for the Best Use of Electrical Current. World Institute of Pain. 5 (2): 74-76. Jun. 2005.
Van De Kraats, Everine B. et al. Noninvasive Magnetic Resonance to Three-Dimensional Rotational X-Ray Registration of Vertebral Bodies for Image-Guided Spine Surgery. Spine. 29 (3): 293-297. Feb. 2004.
Van Kleef, M. et al. Effects and Side Effects of a Percutaneo Thermal Lesion of the Dorsal Root Ganglion in Patients with Cervical Pain Syndrome. Pain. 52 (1): 49-53. Jan. 1993.
Van Kleef, M. et al. Radiofrequency Lesion Adjacent to the Dorsal Root Ganglion for Cervicobrachial Pain: A Prospective Double Blind Randomized Study. Neurosurgery. 38 (6): 1127-31. Jun. 1996.
Van Kleef, Maarten et al. Chapter 160: Radiofrequency Lesions in the Treatment of Pain of Spinal Origin (pp. 1585-1599). Textbook of Stereotactic and Functional Neurosurgery 1st Edition. (Philip L. Gildenberg et al. eds.). New York: McGraw-Hill. (month unavailable) 1998.
Van Zundert, J. et al. Pulsed and Continuous Radiofrequency Current Adjacent to the Cervical Dorsal Root Ganglion of the Rat Induces Late Cellular Activity in the Dorsal Horn. Anesthesiology. 102 (1): 125-31. Jan. 2005.
Vaughan, R. Percutaneous Radiofrequency Gangliotomy in the Treatment of Trigeminal Neuralgia and Other Facial Pain. Aust N Z J Surg. 45 (2): 203-7. May 1975. (Abstract Only).
Viton, J.-M. et al. Short-Term Assessment of Periradicular Corticosteroid Injections in Lumbar Radiculopathy Associated With Disc Pathology. Neuroradiology. 40 (1): 59-62. Jan. 1998.
Viton, J.M. et al. Short-Term Evaluation of Periradicular Corticosteroid Injections in the Treatment of Lumbar Radiculopathy Associated With Disc Disease. Rev Rhum Engl Ed. 65 (3): 195-200. Mar. 1998. (Abstract Only).
Wagner, A.L. et al. Selective Nerve Root Blocks. Tech Vasc Interv Radiol. 5 (4): 194-200. Dec. 2002. (Abstract Only).
Waxman et al.; Sodium channels, excitability of primary sensory neurons, and the molecular basis of pain; Muscle Nerve; 22(9); pp. 1177-1187; Sep. 1999.
Weiner, Richard L. The Future of Peripheral Nerve Neurostimulation. Neurological Research. 22 (3): 299-304. Apr. 2000.
Weiner, Richard L. Peripheral Nerve Neurostimulation. Neurosurgery Clinics of North America. 14 (3): 401-408. Jul. 2003.
Weinstein, James et al. The Pain of Discography. Spine. 13 (12):1344-8. Dec. 1988.
Wessels et al.; A rostrocaudal somatotopic organization in the brachial dorsal root ganglia of neonatal rats; Clin Neurol Neurosurg; 95 Suppl; pp. S3-S11; (month unavailable) 1993.
Wessels et al.; Evidence for a rostrocaudal organization in dorsal root ganglia during development as demonstrated by intra-uterine WGA-HRP injections into the hindlimb of rat fetuses; Brain Res Dev Brain Res; 54(2); pp. 273-281; Jul. 1, 1990.
Wessels et al.; Somatotopic organization in the sensory innervation of the rat hindlimb during development, using half dorsal root ganglia as subsegmental units; Eur J Morphol; 28(2-4); pp. 394-403; (month unavailable) 1990.
Wessels et al.; The rostrocaudal organization in the dorsal root ganglia of the rat: a consequence of plexus formation?; Anat Embryol (Berl); 190(1); pp. 1-11; Jul. 1994.
Wetzel, F. Todd et al. Extradural Sensory Rhizotomy in the Management of Chronic Lumbar Radiculopathy: A Minimum 2-Year Follow-up Study. Spine. 22 (19): 2283-2291. Oct. 1, 1997.
Wetzel, F.T. Chronic Benign Cervical Pain Syndromes: Surgical Considerations. Spine. 17 (10 Suppl): S367-74. Oct. 1992. (Abstract Only).
Wetzel, F.T. et al. The Treatment of Chronic Extremity Pain in Failed Lumbar Surgery. The Role of Lumber Sympathectomy. Spine. 17 (12): 2367-8. Dec. 1992. (Abstract Only).
White, P.F. et al. The Use of a Continuous Popliteal Sciatic Nerve Block After Surgery Involving the Foot and Ankle: Does It Improve the Quality of Recovery? Anesth Analg. 97 (5): 1303-9. Nov. 2003. (Abstract Only).
Whitworth, Louis Anthony et al. Application of Spinal Ablative Techniques for the Treatment of Benign Chronic Painful Conditions. Spine. 27 (22): 2607-2612. Nov. 15, 2002.
Wilkinson, H.A. et al. Sensory Ganglionectomy: Theory, Technical Aspects, and Clinical Experience. J Neurosurg. 95(1): 61-6. Jul. 2001. (Abstract Only).
Wong, C.B. et al. Clinical Outcomes of Revision Lumbar Spinal Surgery: 124 Patient With a Minimum of Two Years of Follow-Up. Chang Gung Med J. 25 (3): 175-82. Mar. 2002. (Abstract Only).
Wright, Robert E. et al. Neurostimulation of the L2 Dorsal Root Ganglion for Intractable Disc Pain: Description of a Novel Technique. Presented at the IFESS. (month unavailable) 1998.
Wu, Gang et al. Early Onset of Spontaneous Activity in Uninjured C-Fiber Nociceptors After Injury to Neighboring Nerve Fibers. Journal of Neuroscience. 21 (8): RC140. Apr. 15, 2001.
Yamashita, Toshihiko et al. A Quantitative Analysis of Sensory Function in Lumbar Radiculopathy Using Current Perception Threshold Testing. Spine. 27 (14): 1567-1570. Jul. 15, 2002.
Yoshida, Hirotoshi et al. Lumbar Nerve Root Compression Caused by Lumbar Intraspinal Gas: Report of Three Cases. Spine. Feb. 1, 1997, vol. 22 (3): 348-351.
Young, R.F. Chapter 161: Dorsal Rhizotomy and Dorsal Root Ganglionectomy (pp. 3442-3451). Neurological Surgery 4th Edition. Jan. 15, 1996. (Julian R. Youmans ed.). Philadelphia: W.B. Saunders Company.
CIPOLLA—The Cerebral Circulation,Chap. 3—Perivascular Innervation ; Morgan & Claypool Life Sciences; San Rafael, Ca.; 1(1):pp. 3; Jan. 2009.
Dorsal Root Ganglion; www.biology-online.org/dDorsal_root_ganglion; downloaded Nov. 5, 2013; 4 pgs.
The Peripheral Nervous System; http://cnx.org/content/m44751/latest; downloaded Nov. 5, 2013; 7 pgs.
Kramer; U.S. Appl. No. 14/362,543 entitled "Neuromodulation of subcellular structures within the dorsal root ganglion," filed Jun. 3, 2014.

(56) References Cited

OTHER PUBLICATIONS

Horsch, S. et al. Epidural spinal cord stimulation in the treatment of severe peripheral arterial occlusive disease; Annals of Vascular Surgery; 8(5): 468-74. Sep. 1994.

Mayfield Clinic for Brain & Spine; printed from http://www.mayfieldclinic.com/PE-AnatSpine.htm (last updated Jan. 2013); 7 pages.

medicinenet.com; Definition of Lateral; printed from http://www.medterms.com/script/main/art.asp?articlekey=6226 (on Jun. 4, 2014); 3 pages.

Kishawi et al.; U.S. Appl. No. 14/615,281 entitled "Pain management with stimulation subthreshold to paresthesia," filed Feb. 5, 2015.

Burdulis; U.S. Appl. No. 14/633,060 entitled "Hard tissue anchors and delivery devices," filed Feb. 26, 2015.

Imran et al.; U.S. Appl. No. 14/719,076 entitled "Sutureless lead retention features," filed May 21, 2015.

Kishawi et al.; U.S. Appl. No. 14/726,359 entitled "Selective stimulation systems and signal parameters for medical conditions," filed May 29, 2015.

* cited by examiner

DEVICES, SYSTEMS AND METHODS FOR THE TARGETED TREATMENT OF MOVEMENT DISORDERS

CROSS-REFERENCES TO RELATED APPLICATIONS

This application is a continuation-in-part of and claims priority to U.S. patent application Ser. No. 12/607,009 filed on Oct. 27, 2009 now U.S. Pat. No. 9,056,197 and this application claims priority under 35 U.S.C. 119(e) to U.S. Provisional Patent Application Ser. No. 61/438,895 filed on Feb. 2, 2011, both of which are incorporated herein by reference in their entirety.

STATEMENT AS TO RIGHTS TO INVENTIONS MADE UNDER FEDERALLY SPONSORED RESEARCH AND DEVELOPMENT

NOT APPLICABLE

REFERENCE TO A "SEQUENCE LISTING," A TABLE, OR A COMPUTER PROGRAM LISTING APPENDIX SUBMITTED ON A COMPACT DISK

NOT APPLICABLE

BACKGROUND

Movement disorders are neurological conditions that affect the ability to produce and control body movement. In particular, such disorders interfere with the speed, fluency, quality, and ease of movement. And, in some cases, cognitive and autonomic functions can be affected. Currently it is estimated that over 40 million individuals suffer from some sort of movement disorders. They can occur in all age groups from infancy to the elderly.

Treatment for movement disorders depends on the underlying cause. In most cases, the goal of treatment is to relieve symptoms. Treatment may include medication, botulinum toxin injection therapy, and surgery. Medications that are typically used include the following: antiepileptics, antiseizure medications, beta-blockers, dopamine agonists, and tranquilizers. However, these medications have a variety of side effects. Side effects of antiepileptics include dizziness, drowsiness, nausea, and vomiting. Antiseizure medications may cause a lack of coordination and balance (ataxia), dizziness, nausea, and fatigue. Side effects caused by beta-blockers include slowed heart rate (bradycardia), depression, lightheadedness, and nausea. Dopamine agonists may cause nausea, headache, dizziness, and fatigue. Tranquilizers such as benzodiazepines may cause blood clots (thrombosis), drowsiness, and fatigue.

Botulinum toxin injection therapy is used to treat some types of movement disorders (e.g., spasmodic torticollis, blepharospasm, myoclonus, tremor). In this treatment, a potent neurotoxin (produced by the bacterium Clostridium botulinum) is injected into a muscle to inhibit the release of neurotransmitters that cause muscle contraction. In some cases, treatment is repeated every 3 to 4 months. However, patients may develop antibodies to the toxin over time, causing treatment to become ineffective. Side effects include temporary weakness in the group of muscles being treated, unintentional paralysis of muscles other than those being treated and rarely, flu-like symptoms.

When medication is ineffective, severe movement disorders may require surgery. In such instances, deep brain stimulation may be performed wherein a surgically implanted neurostimulator is used to deliver electrical stimulation to areas of the brain that control movement. The electrical charge blocks nerve signals that trigger abnormal movement. In deep brain stimulation, a lead is inserted through a small incision in the skull and is implanted in the targeted area of the brain. An insulated wire is then passed under the skin in the head, neck, and shoulder, connecting the lead to the neurostimulator, which is surgically implanted in the chest or upper abdomen. However, negative side effects of deep brain stimulation can occur, including: bleeding at the implantation site, depression, impaired muscle tone, infection, loss of balance, slight paralysis (paresis), slurred speech (dysarthia), and tingling (parethesia) in the head or the hands.

Another type of surgical treatment for motion disorders is ablative surgery. Ablative surgery locates, targets, and then destroys (ablates) a defined area of the brain that produces chemical or electrical impulses that cause abnormal movements. In this surgery, a heated probe or electrode is inserted into the targeted area. The patient remains awake during the procedure to determine if the problem has been eliminated. A local anesthetic is used to dull the outer part of the brain and skull. The brain is insensitive to pain, so the patient does not feel the actual procedure. However, in some cases, it may be difficult to estimate how much tissue to destroy and the amount of heat to use. This type of surgery involves either ablation in the part of the brain called the globus pallidus (called pallidotomy) or ablation of brain tissue in the thalamus (called thalamotomy). Pallidotomy may be used to eliminate uncontrolled dyskinesia (e.g., jerky, involuntary movements) and thalamotomy may be performed to eliminate tremor. A related procedure, cryothalamotomy, uses a supercooled probe that is inserted into the thalamus to freeze and destroy areas that produce tremors.

Aside from the risks and side effects associated with the above described therapies, such treatments are not always effective in treating the movement disorder. Therefore, improved therapies with higher effectiveness and lower side effects are desired. At least some of these objectives will be met by the following invention.

SUMMARY OF THE DISCLOSURE

In a first aspect of the invention, a method is provided treating a patient having a movement disorder. In some embodiments, the method comprises presenting the patient having the movement disorder, positioning a lead having at least one electrode within the patient so that the at least one electrode is disposed near a target dorsal root ganglion associated with the movement disorder, and providing stimulation energy to the at least one electrode so as to selectively stimulate at least a portion of the target dorsal root ganglion so as to reduce a symptom of the movement disorder while providing no or imperceptible amounts of stimulation energy directly to a ventral root. In some embodiments, the movement disorder includes Parkinson's Disease, Multiple Sclerosis or a Demylenating Movement Disorder. In other embodiments, the movement disorder includes Cerebral Palsy, Chorea, Dystonia, Spasm, Tic disorder or Tremor. It may be appreciated that other movement disorders may also be treated with the methods and devices of the present invention.

In some embodiments, the target dorsal root ganglion is associated with a reflex arc and providing stimulation energy comprises activating the reflex arc. In some instances, activating the reflex arc comprises stimulating at least one sensory neuron so as to activate at least one soma of an alpha motor neuron. In some embodiments, the at least one sensory neuron comprises an Ia sensory fiber. In other embodiments, the at least one sensory neuron comprises an Ib sensory fiber.

In some embodiments, providing stimulation energy comprises providing a stimulation signal having at least one parameter selected to selectively stimulate the at least a portion of the target dorsal root ganglion so as to reduce a symptom of the movement disorder. In some instances, the at least one parameter comprises frequency. Optionally, the at least one parameter comprises frequency having a value of less than or equal to approximately 100 Hz.

In some embodiments, providing stimulation energy comprises choosing size of the at least one electrode, shape of the at least one electrode, and/or position of the at least one electrode so as to selectively stimulate the at least a portion of the target dorsal root ganglion so as to reduce the symptom of the movement disorder.

In some embodiments, providing stimulation energy comprises providing stimulation energy in response to at least one sensor configured to sense an indicator of the movement disorder. In some instances, the indicator comprises an onset of the symptom of the movement disorder, and the stimulation signal is provided to reduce or avoid the onset of the symptom. In some instances, the indicator comprises a status of the symptom of the movement disorder, and the stimulation signal is provided to treat the symptom in real time.

In some embodiments, providing stimulation energy comprises providing stimulation energy in response to at least one sensor configured to sense an activity or an activity level of the patient.

In some embodiments, providing stimulation energy comprises providing stimulation energy in response to at least one sensor configured to detect a position of at least a portion of a body of the patient.

In second aspect of the invention, a method is provided of treating a movement disorder of a patient comprising advancing a sheath having a curved distal end along an epidural space of the patient, positioning the curved distal end so as to direct a lead advanced therethrough toward a spinal nerve associated with the disorder, advancing the lead having at least one electrode through the sheath so that the at least one electrode is disposed near the spinal nerve, and providing stimulation energy to the at least one electrode so as to stimulate at least a portion of the spinal nerve in a manner which reduces a symptom of the movement disorder. In some instances, the movement disorder includes Parkinson's Disease, Multiple Sclerosis or a Demylenating Movement Disorder. In other instances, the movement disorder includes Cerebral Palsy, Chorea, Dystonia, Spasm, Tic disorder or Tremor. It may be appreciated that other movement disorders may also be treated with the methods and devices of the present invention.

In some embodiments, the at least a portion of the spinal nerve comprises at least a portion of a dorsal root ganglion associated with the movement disorder. And, in some embodiments, providing stimulation energy comprises adjusting at least one signal parameter to reduce the symptom of the movement disorder. In some instances, adjusting the at least one signal parameter comprises adjusting a frequency of the stimulation energy. For example, adjusting a frequency of the stimulation energy may comprise selecting a frequency less than or equal to approximately 100 Hz. Or, adjusting a frequency of the stimulation energy may comprise selecting a frequency less than or equal to approximately 50 Hz.

In a third aspect of the invention, a stimulation system is provided for treating a patient having a movement disorder. In some embodiments, the system comprises a lead having at least one electrode, wherein the lead is configured for implantation so as to position at least one of the at least one electrode adjacent a dorsal root ganglion associated with the movement disorder, and a pulse generator electrically connected to the at least one of the at least one electrode, wherein the pulse generator provides a signal to the at least one of the at least one electrode which stimulates at least a portion of the dorsal root ganglion so as to reduce a symptom of the movement disorder.

In some embodiments, the target dorsal root ganglion is associated with a reflex arc and the signal is configured to activate the reflex arc. In some instances, activation of the reflex arc comprises stimulation of at least one sensory neuron so as to activate at least one soma of an alpha motor neuron. In some instances, the at least one sensory neuron comprises an Ia sensory fiber. In other instances, the at least one sensory neuron comprises an Ib sensory fiber.

In some embodiments, the at least of the at least one electrode has a size that selectively stimulates the at least one sensory neuron. In some embodiments, the at least of the at least one electrode has a shape that selectively stimulates the at least one sensory neuron.

In some embodiments, the signal has at least one parameter that is programmable to selectively stimulate the at least one sensory neuron. In some instances, the at least one parameter comprises frequency. In some instances, the frequency is programmable with a value up to approximately 100 Hz. In other instances, the frequency is programmable with a value up to approximately 50 Hz.

In some embodiments the stimulation system further comprises at least one sensor configured to sense an indicator of the movement disorder. In some embodiments, the at least one sensor comprises an accelerometer, a strain gauge, or an electrical device which measures electrical activity in a muscle or nerve. In some embodiments, the indicator indicates an onset of the symptom of the movement disorder, and the stimulation signal is provided to reduce or avoid the onset of the symptom. In some embodiments, the indicator indicates a status of the symptom of the movement disorder, and the stimulation signal is provided to treat the symptom in real time. In some embodiments, the indicator indicates a position of at least a portion of a body of the patient.

In some embodiments, the stimulation system further comprises at least one sensor configured to sense an activity or an activity level of the patient.

In a fourth aspect of the invention, a system is provided for treating a patient having a movement disorder, the system comprising a lead having at least one electrode, wherein the lead is configured to be positioned so that at least one of the at least one electrodes is able to stimulate at least a portion of a target dorsal root associated with the movement disorder, at least one sensor configured to sense a symptom of the movement disorder, and an implantable pulse generator connectable with the lead, wherein the generator includes electronic circuitry configured to receive information from the at least one sensor and provide a stimulation signal to the lead in response to the sensed symptom of the movement disorder, wherein the stimulation signal has an energy below an energy threshold for stimulating a ventral root associated with the target dorsal root while the lead is so positioned.

In some embodiments, the at least one sensor senses an onset of the symptom of the movement disorder, and the stimulation signal is provided to reduce or avoid the onset of the symptom.

In some embodiments, the at least one sensor senses a status of the symptom of the movement disorder, and wherein the stimulation signal is provided to treat the symptom in real time.

In some embodiments, the at least one sensor senses an activity or an activity level of the patient.

In some embodiments, the at least one sensor detects a position of at least a portion of a body of the patient.

In some embodiments, the at least one sensor comprises an accelerometer, a strain gauge, or an electrical device which measures electrical activity in a muscle or nerve.

Other objects and advantages of the present invention will become apparent from the detailed description to follow, together with the accompanying drawings.

DETAILED DESCRIPTION

Figure 1:
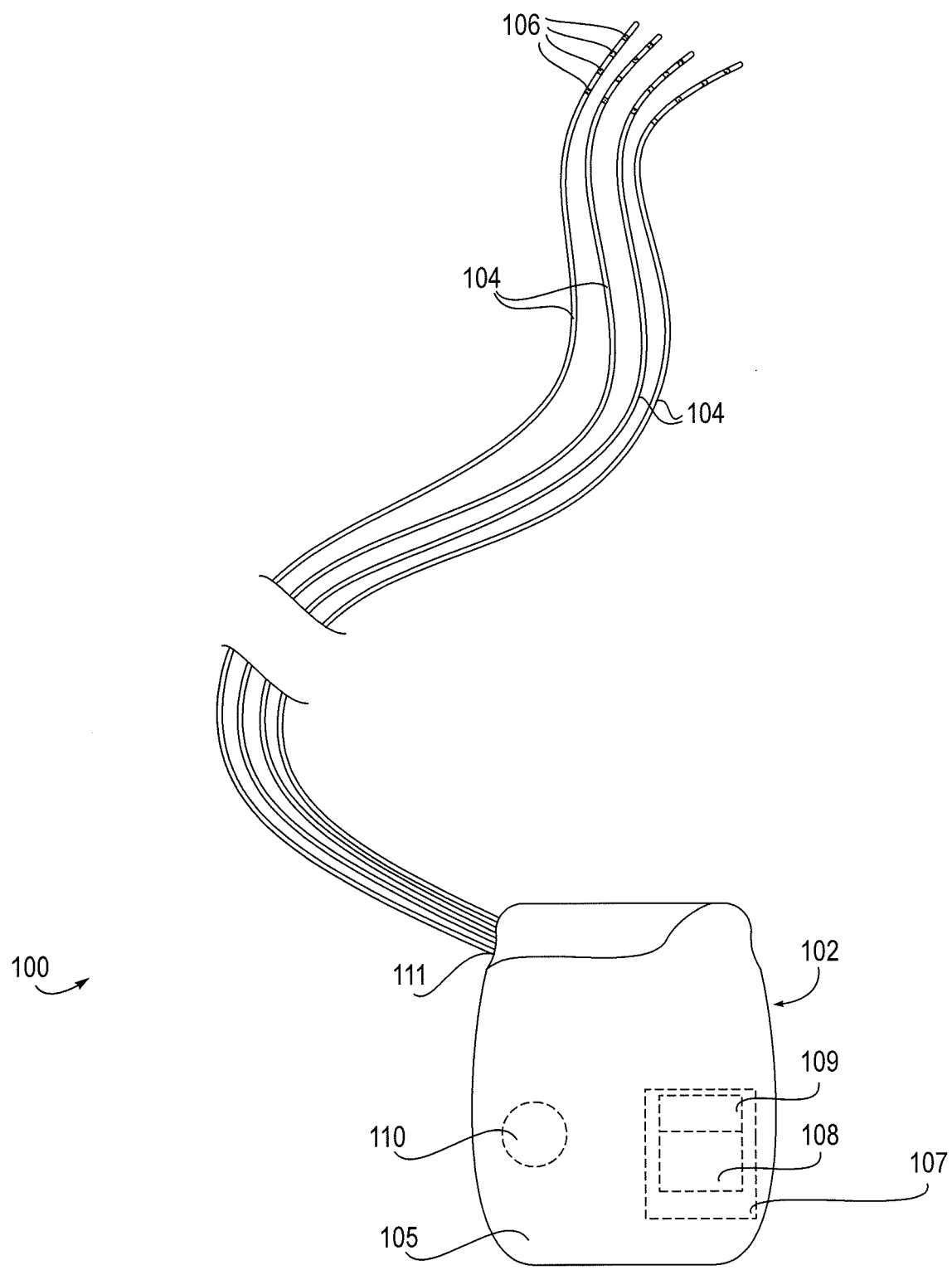
FIG. 1 illustrates an embodiment of an implantable stimulation system.

The present invention provides devices, systems and methods for the targeted treatment of movement disorders. Such movement disorders include, among others,
1) Akathisia
2) Akinesia (lack of movement)
3) Associated Movements (Mirror Movements or Homolateral Synkinesis)
4) Athetosis (contorted torsion or twisting)
5) Ataxia
6) Ballismus (violent involuntary rapid and irregular movements) and Hemiballismus (affecting only one side of the body)
7) Bradykinesia (slow movement)
8) Cerebral palsy
9) Chorea (rapid, involuntary movement), including Sydenham's chorea, Rheumatic chorea and Huntington's disease
10) Dystonia (sustained torsion), including Dystonia muscularum, Blepharospasm, Writer's cramp, Spasmodic torticollis (twisting of head and neck), and Dopamine-responsive dystonia (hereditary progressive dystonia with diurnal fluctuation or Segawa's disease)
11) Geniospasm (episodic involuntary up and down movements of the chin and lower lip)
12) Myoclonus (brief, involuntary twitching of a muscle or a group of muscles)
13) Metabolic General Unwellness Movement Syndrome (MGUMS)
14) Multiple Sclerosis
15) Parkinson's disease
16) Restless Legs Syndrome RLS (WittMaack-Ekboms disease)
17) Spasms (contractions)
18) Stereotypic movement disorder
19) Stereotypy (repetition)
20) Tardive dyskinesia
21) Tic disorders (involuntary, compulsive, repetitive, stereotyped), including Tourette's syndrome
22) Tremor (oscillations)
23) Rest tremor (approximately 4-8 Hz)
24) Postural tremor
25) Kinetic tremor
26) Essential tremor (approximately 6-8 Hz variable amplitude)
27) Cerebellar tremor (approximately 6-8 Hz variable amplitude)
28) Parkinsonian tremors (approximately 4-8 Hz variable amplitude)
29) Physiological tremor (approximately 10-12 Hz low amplitude)
30) Wilson's disease The present invention provides for targeted treatment of such conditions with minimal deleterious side effects, such as undesired motor responses or undesired stimulation of unaffected body regions. This is achieved by directly neuromodulating a target anatomy associated with the condition while minimizing or excluding undesired neuromodulation of other anatomies. In most embodiments, neuromodulation comprises stimulation, however it may be appreciated that neuromodulation may include a variety of forms of altering or modulating nerve activity by delivering electrical and/or pharmaceutical agents directly to a target area. For illustrative purposes, descriptions herein will be provided in terms of stimulation and stimulation parameters, however, it may be appreciated that such descriptions are not so limited and may include any form of neuromodulation and neuromodulation parameters.

Typically, the systems and devices are used to stimulate portions of neural tissue of the central nervous system, wherein the central nervous system includes the spinal cord and the pairs of nerves along the spinal cord which are known as spinal nerves. The spinal nerves include both dorsal and ventral roots which fuse to create a mixed nerve which is part of the peripheral nervous system. At least one dorsal root ganglion (DRG) is disposed along each dorsal root prior to the point of mixing. Thus, the neural tissue of the central nervous system is considered to include the dorsal root ganglions and exclude the portion of the nervous system beyond the dorsal root ganglions, such as the mixed nerves of the peripheral nervous system. Typically, the systems and devices of the present invention are used to stimulate one or more dorsal root ganglia, dorsal roots, dorsal root entry zones, or portions thereof, while minimizing or excluding undesired stimulation of other tissues, such as surrounding or nearby tissues, ventral root and portions of the anatomy associated with body regions which are not targeted for treatment. However, it may be appreciated that stimulation of other tissues are contemplated.

The target stimulation areas of the present invention, particularly the dorsal root ganglia, are utilized due to their specialized role in movement. It is in these areas that sensory fibers are isolated from motor fibers. Sensory fibers are involved in a variety of reflexes that are involved in movement control, and these reflexes can be utilized in the treatment of various movement disorders. Thus, by stimulating sensory fibers in these areas, fundamental reflexes can be affected to lessen the symptoms of movement disorders. In addition, such targeted stimulation reduces undesired side effects, such as painful tingling or unwanted movements caused by direct stimulation of motor nerves, such as within the ventral root.

A variety of motor reflexes are involved in movement control. A reflex or reflex arc is the neural pathway that mediates a reflex action. A motor reflex action occurs relatively quickly by activating motor neurons in the spinal cord without the delay of routing signals through the brain. Normally, messages from nerve cells in the brain (upper motor neurons) are transmitted to nerve cells in the brain stem and spinal cord (lower motor neurons) and from there to particular muscles. Thus, upper motor neurons direct the lower motor neurons to produce movements such as walking or chewing. Lower motor neurons control movement in the arms, legs, chest, face, throat, and tongue. However, lower motor neurons can be accessed via a reflex arc to circumvent the involvement of upper neurons. This is beneficial when responding to a harmful stimulus, such as a hot surface, wherein speed is critical. And, this is beneficial when there is damage or disease affecting upper neurons resulting in a movement disorder.

The present invention utilizes such reflex arcs to treat patients presenting with one or more movement disorders. FIG. 1 illustrates an embodiment of an implantable stimulation system 100 for treatment of such patients. The system 100 includes an implantable pulse generator (IPG) 102 and at least one lead 104 connectable thereto. In preferred embodiments, the system 100 includes four leads 104, as shown, however any number of leads 104 may be used including one, two, three, four, five, six, seven, eight, up to 58 or more. Each lead 104 includes at least one electrode 106. In preferred embodiments, each lead 104 includes four electrodes 106, as shown, however any number of electrodes 106 may be used including one, two, three, four five, six, seven, eight, nine, ten, eleven, twelve, thirteen, fourteen, fifteen, sixteen or more. Each electrode can be configured as off, anode or cathode. In some embodiments, even though each lead and electrode are independently configurable, at any given time the software ensures only one lead is stimulating at any time. In other embodiments, more than one lead is stimulating at any time, or stimulation by the leads is staggered or overlapping.

Referring again to FIG. 1, the IPG 102 includes electronic circuitry 107 as well as a power supply 110, e.g., a battery, such as a rechargeable or non-rechargeable battery, so that once programmed and turned on, the IPG 102 can operate independently of external hardware. In some embodiments, the electronic circuitry 107 includes a processor 109 and programmable stimulation information in memory 108.

Figure 2:
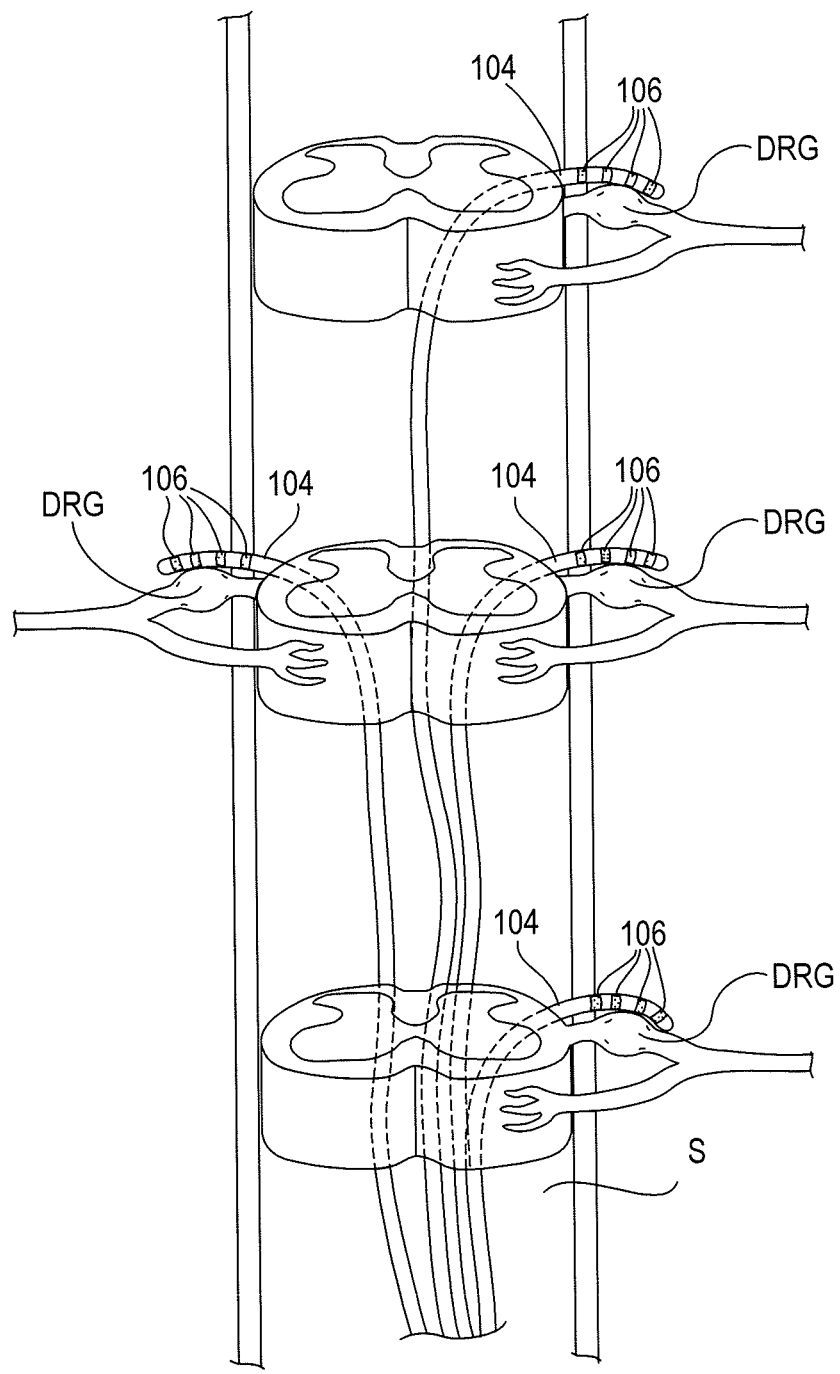
FIG. 2 illustrates example placement of the leads of the embodiment of FIG. 1 within a patient anatomy.

The implantable stimulation system 100 can be used to stimulate a variety of anatomical locations within a patient's body. In preferred embodiments, the system 100 is used to stimulate one or more dorsal roots, particularly one or more dorsal root ganglions. FIG. 2 illustrates example placement of the leads 104 of the embodiment of FIG. 1 within the patient anatomy. In this example, each lead 104 is individually advanced within the spinal column S in an antegrade direction. Each lead 104 has a distal end which is guidable toward a target DRG and positionable so that its electrodes 106 are in proximity to the target DRG. Specifically, each lead 104 is positionable so that its electrodes 106 are able to selectively stimulate the DRG, either due to position, electrode configuration, electrode shape, electric field shape, stimulation signal parameters or a combination of these. FIG. 17 illustrates the stimulation of four DRGs, each DRG stimulated by one lead 104. These four DRGs are located on three levels, wherein two DRGs are stimulated on the same level. It may be appreciated that any number of DRGs and any combination of DRGs may be stimulated with the stimulation system 100 of the present invention. It may also be appreciated that more than one lead 104 may be positioned so as to stimulate an individual DRG and one lead 104 may be positioned so as to stimulate more than one DRG.

Figure 3:
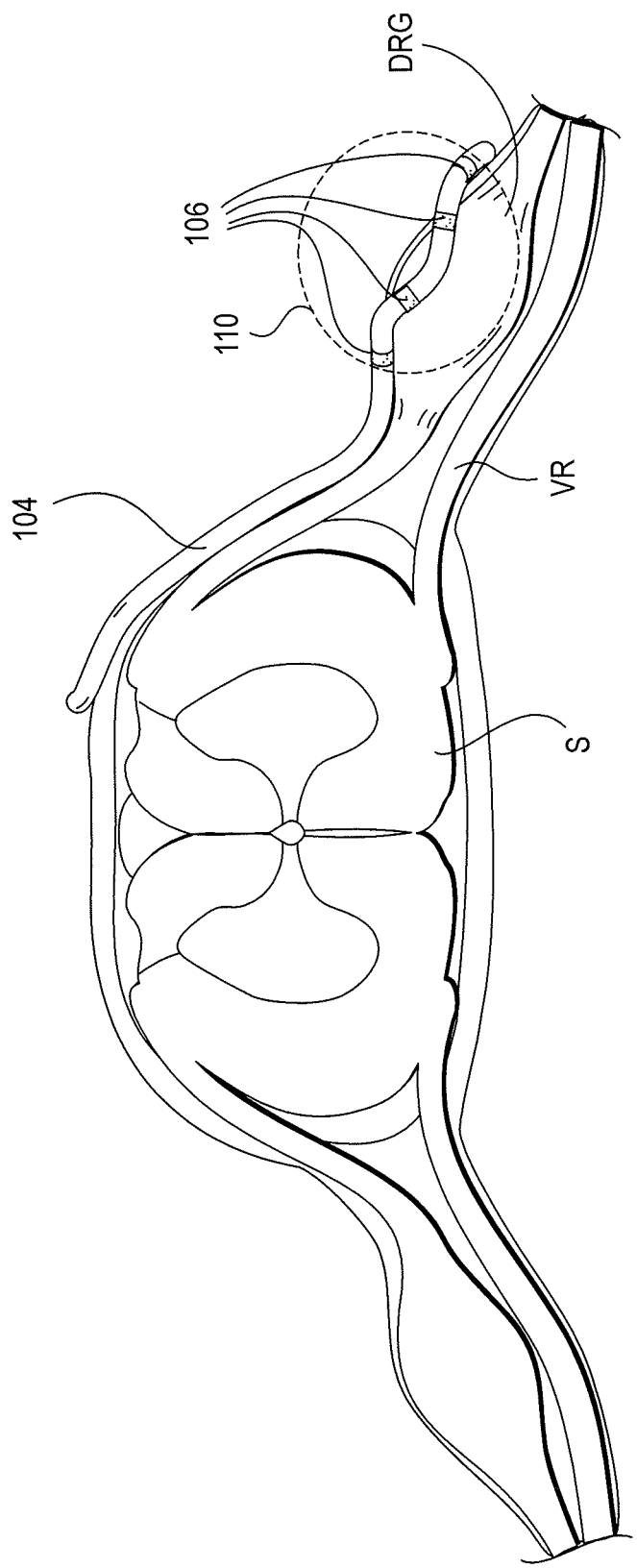
FIG. 3 illustrates an example cross-sectional view of an individual spinal level showing a lead positioned on, near or about a target dorsal root ganglion.

FIG. 3 illustrates an example cross-sectional view of an individual spinal level showing a lead 104 of the stimulation system 100 positioned on, near or about a target DRG. The lead 104 is advanced along the spinal cord S to the appropriate spinal level wherein the lead 104 is advanced laterally toward the target DRG. In some instances, the lead 104 is advanced through or partially through a foramen. At least one, some or all of the electrodes 106 are positioned on, about or in proximity to the DRG. In preferred embodiments, the lead 104 is positioned so that the electrodes 106 are disposed along a surface of the DRG opposite to the ventral root VR, as illustrated in FIG. 3. It may be appreciated that the surface of the DRG opposite the ventral root VR may be diametrically opposed to portions of the ventral root VR but is not so limited. Such a surface may reside along a variety of areas of the DRG which are separated from the ventral root VR by a distance.

In some instances, such electrodes 106 may provide a stimulation region indicated by dashed line 110, wherein the DRG receives stimulation energy within the stimulation region and the ventral root VR does not as it is outside of the stimulation region. Thus, such placement of the lead 104 may assist in reducing any possible stimulation of the ventral root VR due to distance. However, it may be appreciated that the electrodes 106 may be positioned in a variety of locations in relation to the DRG and may selectively stimulate the DRG due to factors other than or in addition to distance, such as due to stimulation profile shape and stimulation signal parameters, to name a few. It may also be appreciated that the target DRG may be approached by other methods, such as a retrograde epidural approach. Likewise, the DRG may be approached from outside of the spinal column wherein the lead 104 is advanced from a peripheral direction toward the spinal column, optionally passes through or partially through a foramen and is implanted so that at least some of the electrodes 106 are positioned on, about or in proximity to the DRG.

In order to position the lead 104 in such close proximity to the DRG, the lead 104 is appropriately sized and configured to maneuver through the anatomy. In some embodiments, such maneuvering includes atraumatic epidural advancement along the spinal cord S, through a sharp curve toward a DRG, and optionally through a foramen wherein the distal end of the lead 104 is configured to then reside in close proximity to a small target such as the DRG. Consequently, the lead 104 is significantly smaller and more easily maneuverable than conventional spinal cord stimulator leads. Example leads and delivery systems for delivering the leads to a target such as the DRG are provided in U.S. patent application Ser. No. 12/687, 737, entitled "Stimulation Leads, Delivery Systems and Methods of Use", incorporated herein by reference for all purposes. In one embodiment, an introducing needle is used to access the epidural space of the spinal cord S. The needle has a hollow shaft and typically has a very slightly curved distal end. The shaft is sized to allow passage of the lead, sheath and stylet therethrough. In some embodiments, the needle is 14 gauge which is typically the size of epidural needles used to place conventional percutaneous leads within the epidural space. However, it may be appreciated that other sized needles may also be used, particularly smaller needles such as 15-18 gauge. Alternatively, non-standardized sized needles may be used.

Figure 4:
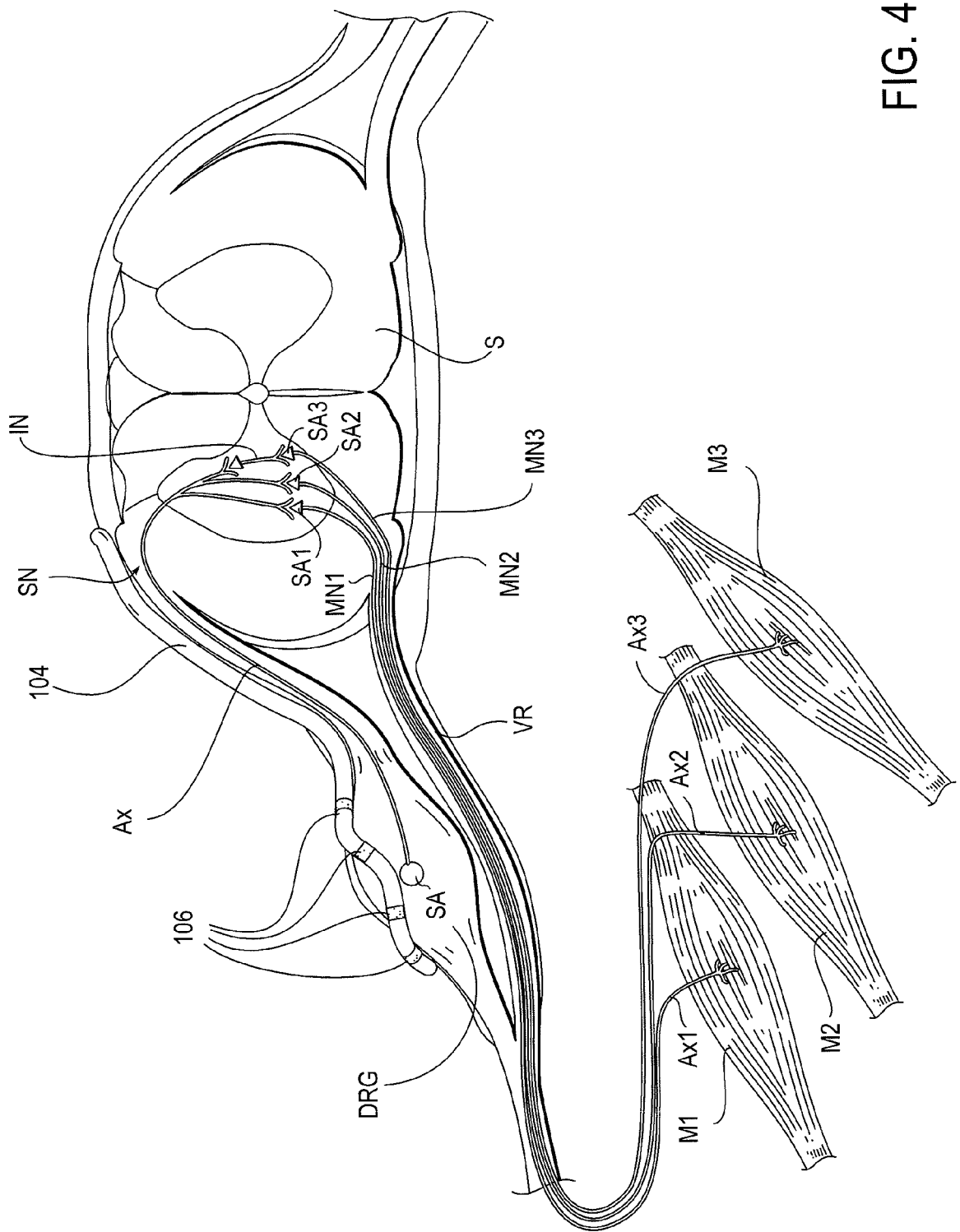
FIGS. 4-5 illustrates example activation of reflex arc in the treatment of movement disorders.

FIG. 4 illustrates the lead 104 positioned near a DRG so as to activate an example reflex arc in the treatment of a movement disorder. In this example, the reflex arc includes a sensory neuron SN, which includes a soma SA disposed within the DRG and an axon AX which extends through the dorsal root DR to the dorsal horn of the spinal cord S. The sensory neuron SN connects with a variety of motor neurons MN and interconnector neurons IN within the spinal cord S. In this example, the sensory neuron SN connects with two motor neurons MN1, MN2 and an interconnector neuron IN which connects with motor neuron MN3. Motor neuron MN1 (an alpha motor neuron) includes a soma SA1 disposed within the ventral horn of the spinal cord S and an axon AX1 which extends through the ventral root VR and innervates a skeletal muscle M1, such as a flexor muscle. Motor neuron MN2 (a second alpha motor neuron) includes a soma SA2 disposed within the ventral horn of the spinal cord S and an axon AX2 which extends through the ventral root VR and innervates a skeletal muscle M2 which is synergistic with muscle M1. Motor neuron MN3 (a third alpha motor neuron) includes a soma SA3 disposed within the ventral horn of the spinal cord S and an axon AX3 which extends through the ventral root VR and innervates a skeletal muscle M3 which is antagonistic to muscle M1 and muscle M2.

In many movement disorders, improper action potentials are generated, either from damage to the upper motor neurons or from other causes. In some instances, such improper action potentials cause muscles (such as muscle MD and synergistic muscles (such as M2) to undesirably contract while causing antagonistic muscles (such as muscle M3) to undesirably relax. In some embodiments, treatment of such a condition is achieved by providing selective stimulation to the dorsal root and/or DRG associated with the muscles M1, M2, M3, with the use of an appropriately positioned lead 104, as illustrated in FIG. 4. As mentioned previously, at least one, some or all of the electrodes 106 are positioned on, about or in proximity to the target DRG. In some embodiments, the involved sensory neuron SN, particularly its soma SA within the target DRG, is selectively stimulated so as to inhibit the improper action potentials causing muscles M1, M2 to contract and muscle M3 to relax. This is particularly the case when the involved sensory neuron SN is an Ia sensory fiber. Such stimulation reduces the symptoms of the movement disorder in treatment of the condition.

In some embodiments, selective stimulation of the involved sensory neuron SN is achieved with the choice of the size of the electrode(s), the shape of the electrode(s), the position of the electrode(s), the stimulation signal, pattern or algorithm, or any combination of these. Such selective stimulation stimulates the targeted neural tissue while excluding untargeted tissue, such as surrounding or nearby tissue. In some embodiments, the stimulation energy is delivered to the targeted neural tissue so that the energy dissipates or attenuates beyond the targeted tissue or region to a level insufficient to stimulate modulate or influence such untargeted tissue. In particular, selective stimulation of tissues, such as the dorsal root, DRG, or portions thereof, exclude stimulation of the ventral root wherein the stimulation signal has an energy below an energy threshold for stimulating a ventral root associated with the target dorsal root while the lead is so positioned. Examples of methods and devices to achieve such selective stimulation of the dorsal root and/or DRG are provided in U.S. patent application Ser. No. 12/607,009, entitled "Selective Stimulation Systems and Signal Parameters for Medical Conditions", incorporated herein by reference for all purposes. It may be appreciated that indiscriminant stimulation of the ventral root, such as from an electrode which emits stimulation energy which directly stimulates the ventral root, typically causes unpleasant sensations for the patient, such as tingling, buzzing or undesired motions or movements. Therefore, it is desired to stimulate motor neurons M1, M2 and/or M3 via synapses in the spinal cord rather than directly via the ventral root.

It may be appreciated that even though the motor neurons are stimulated via synapses in the spinal cord, such stimulation is differentiated from stimulating the spinal cord directly to affect motor neurons. The spinal cord is a highly innervated portion of the anatomy; sensory information from receptors throughout most of the body is relayed to the brain by means of ascending tracts of fibers that conduct impulses up the spinal cord, and, the brain directs motor activities in the form of nerve impulses that travel down the spinal cord in descending tracts of fibers. The white matter of the spinal cord is composed of ascending and descending fiber tracts. These are arranged into six columns of white matter called funiculi. The ascending fiber tracts convey sensory information from cutaneous receptors, proprioceptors (muscle and joint senses), and visceral receptors. The descending fiber tracts convey motor information, and there are two major groups of descending tracts from the brain: the corticospinal, or pyramidal tracts, and the extrapyramidal tracts.

From 80%-90% of the corticospinal fibers decussate in the pyramids of the medulla oblongata (hence the name "pyramidal tracts") and descend in the lateral corticospinal tracts, which decussate in the spinal cord. Because of the crossing of fibers, the right cerebral hemisphere controls the musculature on the left side of the body, where the left hemisphere controls the right musculature. The corticospinal tracts are primarily concerned with the control of fine movement that requires dexterity.

Given the high number of fiber tracts within the spinal cord and the extensive crossing of fibers, direct stimulation of the spinal cord typically yields highly variable and/or non-specific generalized results. Slight changes in position of the stimulation electrodes on the spinal cord causes stimulation of different tracts which can easily lead to undesired side effects. For example, given that both sensory and motor information is conveyed within the spinal cord, attempts at stimulating the motor fiber tract often causes inadvertent stimulation of the sensory fiber tract. Likewise, given the interconnectivity of pathways across various spinal levels within the spinal cord, targeting of a particular spinal level or a particular pair of opposing muscle groups is very difficult when applying stimulation to the spinal cord. Further, a higher frequency signal and a higher level of power is also typically required in attempts to reach specific nerve types with stimulation when directly stimulating the spinal cord.

By stimulating the motor neurons in the spinal cord via the dorsal root ganglion, the drawbacks associated with direct stimulation of the spinal cord are avoided. In particular, since the dorsal root ganglion houses primarily sensory neurons, rather than mixed neurons such as in the spinal cord or peripheral nerves, inadvertent stimulation of unrelated or undesired anatomies is obviated. In addition, stimulation of a single dorsal root ganglion only affects muscles that are innervated with motor nerves that synapse with that dorsal root ganglion. Consequently, a single muscle, a single muscle group, pair of opposing muscles or muscle groups or a particular localized area may be precisely targeted by stimulating a corresponding dorsal root ganglion. Such specificity and targeting is beneficial for treating localized spasticity or other such movement disorders, among other conditions. Further, stimulation of a dorsal root ganglion requires less power than comparative stimulation on the spinal cord. And, stimulation of the dorsal root ganglion involves a lower frequency than comparative stimulation of the spinal cord. In some embodiments, a low frequency signal is used, particularly a frequency less than or equal to approximately 100 Hz, more particularly less than or equal to approximately 80 Hz, and more particularly 4-80 Hz. In some embodiments, the signal has a frequency of approximately less than or equal to 70 Hz, 60 Hz, 50 Hz, 40 Hz, 30 Hz, 20 Hz, 10 Hz, or 5 Hz. It may be appreciated that typically the desired frequency used to treat a movement disorder varies from patient to patient. For example, in one patient a symptom of a movement disorder is reduced with the use of a stimulation signal having a given frequency, such as 100 Hz, by stimulating a particular dorsal root ganglion. And, in another patient having the same or similar movement disorder, a symptom of the movement disorder is reduced with the use of a stimulation signal having a different frequency, such as 50 Hz, by stimulating a corresponding particular dorsal root ganglion. Such variations may be due to slight differences in anatomy between the patients and differences in disease pathology, to name a few. However, it may be appreciated that the frequency is typically in the low frequency range.

Figure 5:
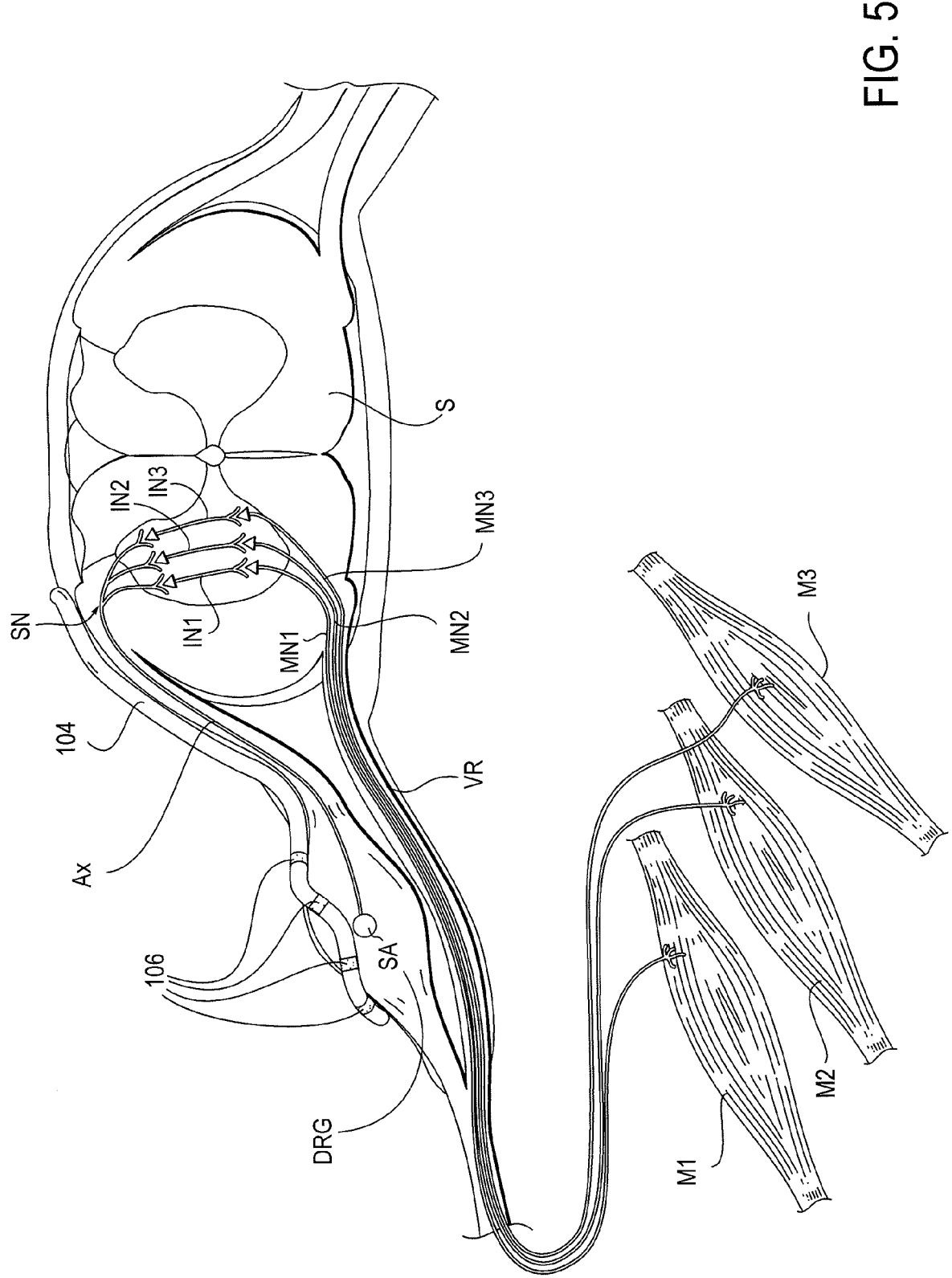

In other instances, improper action potentials due to movement disorders cause muscles (such as muscle M1) and synergistic muscles (such as M2) to undesirably relax while causing antagonistic muscles (such as muscle M3) to undesirably contract. In some embodiments, treatment of such a condition is achieved by providing selective stimulation to the dorsal root and/or DRG associated with the muscles M1, M2, M3, with the use of an appropriately positioned lead 104, as illustrated in FIG. 5. In this example, the reflex arc again includes a sensory neuron SN, which includes a soma SA disposed within the DRG and an axon AX which extends through the dorsal root DR to the dorsal horn of the spinal cord S. The sensory neuron SN connects with a variety of interconnector neurons IN1, IN2, IN3 within the spinal cord S. Interconnector neuron IN1 connects with motor neuron MN1 (an alpha motor neuron) which innervates a skeletal muscle M1, such as a flexor muscle. Interconnector neuron IN2 connects with motor neuron MN2 (a second alpha motor neuron) which innervates a skeletal muscle M2 which is synergistic with muscle M1. Interconnector neuron IN3 connects with motor neuron MN3 (a third alpha motor neuron) which innervates a skeletal muscle M3 which is antagonistic to muscle M1 and muscle M2. As mentioned previously, at least one, some or all of the electrodes 106 are positioned on, about or in proximity to the target DRG. In some embodiments, the involved sensory neuron SN, particularly its soma SA within the target DRG, is selectively stimulated so as to inhibit the improper action potentials causing muscles M1, M2 to relax and muscle M3 to contract. This is particularly the case when the involved sensory neuron SN is an Ib sensory fiber. Such stimulation reduces the symptoms of the movement disorder in treatment of the condition.

In some embodiments, the implantable pulse generator (IPG) 102 comprises circuitry which initiates or modifies the electrical stimulation in response to one or more sensors. Example sensors include, among others, accelerometers, strain gauges, electrical devices which measure electrical activity in muscles and/or nerves, or other devices capable of measuring physiological parameters indicative of symptoms of the movement disorder under treatment. In some embodiments, the one or more sensors sense the onset of symptoms of the movement disorder, transmitting such information to the electronic circuitry 107 of the IPG 102 so that electrical stimulation is provided to the patient to counteract, reduce and/or avoid the onset of symptoms of the movement disorder. For example, in patients suffering from tremors, such tremors may be sudden in onset and remission. Some have increased incidence with stress or decreased incidence when the patient is distracted. This is particularly the case with psychogenic tremors. In such patients, the tremor activity may be sensed with a sensor, such as on a bracelet or anklet worn on the affected limb or limbs. The sensor may sense a change in acceleration of the limb, frequency of movement of the limb, position of the limb, or a combination of these, to name a few. It may be appreciated that such sensors may also be used on other affected areas of the body, such as the head, neck, shoulder, torso, etc. When the tremor activity is sensed as increased, such as an onset or increase in activity, the electrical stimulation is changed to inhibit or diminish the increase in tremor activity. This may be achieved by increasing or decreasing one or more signal parameters, such as amplitude, frequency, pulse width or a combination of these. Likewise, it may be appreciated that when the tremor activity is sensed as decreased, such as a remission or decrease in activity, the electrical stimulation may be changed, such as to more appropriately match the stimulation to the tremor activity. In other instances, stimulation may be changed during remission or decrease in tremor activity to conserve power, prolong battery life, or reduce any side effects or symptoms related to unnecessary or undesired stimulation, to name a few. It may be appreciated that tremor has been used merely as an example and other movement disorders or symptoms related to movement disorders may be similarly sensed. For example, some patients with movement disorders experience jerks or twitches in some part of the body. These jerky movements may be triggered by pain, certain lighting, or even loud noises. The occurrence of these symptoms may be sensed and counteracted in a manner as described above.

In some embodiments, the one or more sensors sense the status of the symptoms of the movement disorder, such as the extent of contraction or limb movement. Such status information is utilized to modify the electrical stimulation to a level which is appropriate to counteract or treat the symptoms of the movement disorder in real time. For example, patients suffering from spasticity have altered skeletal muscle performance in muscle tone involving hypertonia. It is often referred to as an unusual tightness, stiffness, and/or pull of muscles. Spasticity is found in conditions where the brain and/or spinal cord are damaged or fail to develop normally; these include cerebral palsy, multiple sclerosis, spinal cord injury and acquired brain injury including stroke. In some instances, the level of spasticity may increase or decrease, such as over time or with stimulation. In some embodiments, the status of the symptom, such as spasticity, is sensed to determine if a change has occurred. When the symptom is sensed as changed, the electrical stimulation is changed to inhibit or diminish the change in symptom. This may be achieved by increasing or decreasing one or more signal parameters, such as amplitude, frequency, pulse width or a combination of these. Again, it may be appreciated that spasticity has been used merely as an example and other movement disorders or symptoms related to movement disorders may be similarly sensed.

In other embodiments, the one or more sensors sense a specific activity or an activity level of the patient. Some movement disorders are correlated to certain activities, such as walking. For example, functional movement disorders often cause problems in coordinated locomotion or walking. These problems could involve dragging one foot or difficulty balancing while walking. An activity or activity level sensor may be used to detect the type of activity (such as walking) and/or amount or degree of activity (such as slow walk or fast walk). The sensed information could be an input to dynamically modify the stimulation program to determine the appropriate level of stimulation. Alternatively or additionally, different pre-programmed stimulation algorithms may be designed for an individual patient based on that specific patient's pattern of activity. Pre-programmed stimulation algorithms may be stored in an appropriate medium for use by a stimulation system described herein. Conventional transcutaneous programming techniques may also be used to update, modify or remove stimulation algorithms.

In other embodiments, the one or more sensors comprise a position sensor which may be used to detect position of the patient. The position of the patient could be an input to the stimulation control system to dynamically modify the stimulation program to determine the appropriate level of stimulation. One example of such a sensor is a multi-axis accelerometer. A conventional 3 or 4 axis accelerometer could be implanted into a patient or maintained on the patient to provide position, activity, activity level, activity duration or other indications of patient status. The detected indications of patient status could in turn be used in determining stimulation level and pattern. The position sensor can be set up or calibrated once positioned or implanted on or in a person. The calibration aids the sensor in correctly recognizing the persons orientation and activity levels.

In some embodiments, the sensor senses when a patient has lowered to laying or sleeping position. Since most movement disorders rarely occur during sleep, stimulation may be reduced or ceased during sleep to reduce power consumption and extend battery life.

In some embodiments, the sensor senses when a patient has risen to a standing position and stimulation is provided to counteract a symptom of a movement disorder related to standing. For example, orthostatic tremor is characterized by fast (>12 Hz) rhythmic muscle contractions that occur in the legs and trunk immediately after standing. Cramps are felt in the thighs and legs and the patient may shake uncontrollably when asked to stand in one spot. No other clinical signs or symptoms are present and the shaking ceases when the patient sits or is lifted off the ground. The high frequency of the tremor often makes the tremor look like rippling of leg muscles while standing. In such patients, stimulation is provided upon sensing of standing wherein the patient immediately feels relief of such symptoms. When the patient moves to a different position, such as sitting, the stimulation is ceased or reduced to a desired level.

In some embodiments, the sensor senses a particular movement pattern and stimulation is provided to counteract a symptom of a movement disorder related to that particular movement pattern. For example, cerebellar tremor is a slow, broad tremor of the extremities that occurs at the end of a purposeful movement, such as trying to press a button or touching a finger to the tip of one's nose. When such a movement patterns is sensed, stimulation is then provided to counteract the symptom of the movement disorder that follows. Cerebellar tremor is caused by lesions in or damage to the cerebellum resulting from stroke, tumor, or disease such as multiple sclerosis or some inherited degenerative disorder. It can also result from chronic alcoholism or overuse of some medicines. In classic cerebellar tremor, a lesion on one side of the brain produces a tremor in that same side of the body that worsens with directed movement. Cerebellar damage can also produce a "wing-beating" type of tremor called rubral or Holmes' tremor—a combination of rest, action, and postural tremors. The tremor is often most prominent when the affected person is active or is maintaining a particular posture. Thus, a variety of sensors may be used in a complex array of decision making processes as to when and how stimulation is provided or changed for a particular patient.

Optionally, a position sensor is located within the same physical housing as the IPG 102. If desired, the position sensor may be located elsewhere on the body in an implanted location or may be worn externally by the person. Position information from the position and/or activity sensor is provided to the IPG 102 using suitable means including direct connections or percutaneous transmission. Although a number of embodiments are suitable, the preferred mode employs, by way of example and not to be construed as limiting of the present invention, one or more accelerometers to determine patient state including, at least, the ability to sense whether the person is erect or recumbent. Additionally, the position sensor could be adapted to provide an indication of activity or level of activity such as the difference between walking and running. In another embodiment, a position sensor may be positioned to sense specific motion such as activity of a particular part of the body to detect specific movement of a body part or limb that, for example, is being treated for a movement disorder. Using this position sensor embodiment, when the person started activity related to a movement disorder, the sensor would detect such activity and provide the appropriate stimulation. In additional alternatives, the position and/or activity sensor includes one or more multi-axis accelerometers.

In some embodiments, the implantable pulse generator (IPG) 102 comprises circuitry which initiates or modifies the electrical stimulation in response to a timer or clock. Thus, stimulation may be reduced or eliminated during times in which the patient is sleeping or times in which it is determined that the patient desires reduced or no treatment of the movement disorder. Such periods of reduced usage may extend the life of the power supply 110.

As mentioned previously, it may be appreciated that neuromodulation may include a variety of forms of altering or modulating nerve activity by delivering electrical and/or pharmaceutical agents directly to a target area. For illustrative purposes, descriptions herein were provided in terms of stimulation and stimulation parameters, however, it may be appreciated that such descriptions are not so limited and may include any form of neuromodulation and neuromodulation parameters, particularly delivery of agents to the dorsal root ganglion. Methods, devices and agents for such delivery are further described in U.S. patent application Ser. No. 13/309,429 entitled, "Directed Delivery of Agents to Neural Anatomy", incorporated herein by reference.

Although the foregoing invention has been described in some detail by way of illustration and example, for purposes of clarity of understanding, it will be obvious that various alternatives, modifications, and equivalents may be used and the above description should not be taken as limiting in scope of the invention which is defined by the appended claims.

What is claims is:

1. A method of treating a movement disorder of a patient using selective stimulation of a soma within a dorsal root ganglion associated with an involved sensory neuron of the movement disorder, comprising:
    positioning an introducing needle into an epidural space of the patient;
    advancing a sheath through the introducing needle and along the epidural space of the patient to a spinal level having the dorsal root ganglion related to the involved sensory neuron of the movement disorder;
    advancing a lead through the needle and sheath toward the dorsal root ganglion so that the at least one electrode is disposed near the dorsal root ganglion; and
    providing stimulation energy to the at least one electrode so as to stimulate at least a portion of the dorsal root ganglion to access a lower motor neuron via a reflex arc in a manner which reduces a symptom of the movement disorder at least partially caused by damage or disease affecting upper neurons.

2. A method as in claim 1, wherein the movement disorder includes Parkinson's Disease, Multiple Sclerosis or a Demylenating Movement Disorder.

3. A method as in claim 1, wherein the movement disorder includes Cerebral Palsy, Chorea, Dystonia, Spasm, Tic disorder or Tremor.

4. A method as in claim 1, wherein providing stimulation energy comprises adjusting at least one signal parameter to reduce the symptom of the movement disorder.

5. A method as in claim 4, wherein adjusting the at least one signal parameter comprises adjusting a frequency of the stimulation energy.

6. A method as in claim 5, wherein adjusting a frequency of the stimulation energy comprises selecting a frequency less than or equal to approximately 100 Hz.

7. A method as in claim 6, wherein adjusting a frequency of the stimulation energy comprises selecting a frequency less than or equal to approximately 50 Hz.

8. A method as in claim 1 wherein providing stimulation energy comprises adjusting at least one signal parameter provided to the at least one electrode to inhibit improper action potentials directed to the lower motor neuron.

9. A method as in claim 8 wherein the improper action potentials directed to the lower motor neuron causes a synergistic muscle pair involved in the movement disorder to contract.

10. A method as in claim 8 wherein the improper action potentials directed to the lower motor neuron causes an antagonistic muscle involved in the movement disorder to relax.

11. A method as in claim 1 wherein providing stimulation energy comprises adjusting at least one signal parameter provided to the at least one electrode based on an input from one or more sensors configured to sense a status of a symptom of the movement disorder of the patient.

12. A method as in claim 11 wherein the symptom is the onset of the symptoms of the movement disorder.

13. A method as in claim 12, wherein the stimulation signal is provided to reduce or avoid the onset of the symptom.

14. A method as in claim 12, wherein the stimulation signal is provided to treat the symptom in real time.

15. A method as in claim 11 wherein the symptom is the extent of contraction of a synergistic muscle.

16. A method as in claim 11 wherein the symptom is the extent of the relaxation of an antagonistic muscle.

17. A method as in claim 1 further comprising providing stimulation energy to the at least one electrode so as to stimulate at least a portion of the dorsal root ganglion to access a lower motor neuron via a reflex arc while providing no or imperceptible amounts of stimulation energy directly to a ventral root.

18. A method as in claim 1 wherein advancing the lead through the needle and sheath toward the dorsal root ganglion so that the at least one electrode is disposed near the dorsal root ganglion such a portion of the dorsal root ganglion is between the at least one electrode and a ventral root adjacent to the dorsal root ganglion.

19. A method as in claim 1, wherein providing stimulation energy comprises activating the reflex arc.

20. A method as in claim 19, wherein activating the reflex arc comprises stimulating at least one sensory neuron so as to activate at least one soma of an alpha motor neuron.

21. A method as in claim 20, wherein the at least one sensory neuron comprises an Ia sensory fiber.

22. A method as in claim 20, wherein the at least one sensory neuron comprises an Ib sensory fiber.

* * * * *